US008268887B2

(12) United States Patent
Xu

(10) Patent No.: US 8,268,887 B2
(45) Date of Patent: Sep. 18, 2012

(54) DRUG CONJUGATES AND METHODS OF USE THEREOF

(76) Inventor: Feng Xu, Palo Alto, CA (US)

( * ) Notice: Subject to any disclaimer, the term of this patent is extended or adjusted under 35 U.S.C. 154(b) by 349 days.

(21) Appl. No.: 12/576,136

(22) Filed: Oct. 8, 2009

(65) Prior Publication Data

US 2010/0113497 A1     May 6, 2010

Related U.S. Application Data

(60) Provisional application No. 61/103,800, filed on Oct. 8, 2008.

(51) Int. Cl.
| A01N 37/12 | (2006.01) |
| A01N 37/44 | (2006.01) |
| A61K 31/195 | (2006.01) |
| C07C 261/00 | (2006.01) |
| C07C 269/00 | (2006.01) |
| C07C 271/00 | (2006.01) |

(52) U.S. Cl. .......................... 514/561; 560/24; 560/115
(58) Field of Classification Search .................. 514/561; 560/24, 115
See application file for complete search history.

(56) References Cited

U.S. PATENT DOCUMENTS

| 3,625,214 A | 12/1971 | Higuchi |
| 3,845,770 A | 11/1974 | Theeuwes et al. |
| 3,916,899 A | 11/1975 | Theeuwes et al. |
| 4,024,175 A | 5/1977 | Satzinger et al. |
| 4,772,594 A | 9/1988 | Hashimoto et al. |
| 4,789,734 A | 12/1988 | Pierschbacher |
| 4,851,426 A * | 7/1989 | Ladkani et al. ............... 514/420 |
| 4,897,268 A | 1/1990 | Tice et al. |
| 4,906,474 A | 3/1990 | Langer et al. |
| 4,925,673 A | 5/1990 | Steiner et al. |
| 4,992,445 A | 2/1991 | Lawter et al. |
| 5,001,139 A | 3/1991 | Lawter et al. |
| 5,023,252 A | 6/1991 | Hseih |
| 5,075,109 A | 12/1991 | Tice et al. |
| 5,190,029 A | 3/1993 | Byron et al. |
| 5,376,359 A | 12/1994 | Johnson |
| 5,563,175 A | 10/1996 | Silverman et al. |
| 5,776,434 A | 7/1998 | Purewal |
| 5,811,128 A | 9/1998 | Tice et al. |
| 5,814,344 A | 9/1998 | Tice et al. |
| 5,820,883 A | 10/1998 | Tice et al. |
| 5,853,763 A | 12/1998 | Tice et al. |
| 5,928,647 A | 7/1999 | Rock |
| 5,942,252 A | 8/1999 | Tice et al. |
| 6,020,370 A | 2/2000 | Horwell et al. |
| 6,028,214 A | 2/2000 | Silverman et al. |
| 6,103,932 A | 8/2000 | Horwell et al. |
| 6,117,906 A | 9/2000 | Silverman et al. |
| 2003/0087803 A1 | 5/2003 | Yatvin et al. |
| 2004/0242570 A1 | 12/2004 | Nudelman et al. |

FOREIGN PATENT DOCUMENTS

| WO | WO 92/09560 A1 | 6/1992 |
| WO | WO 93/23383 A1 | 11/1993 |
| WO | WO 97/29101 A1 | 8/1997 |
| WO | WO 97/33858 A1 | 9/1997 |
| WO | WO 97/33859 A1 | 9/1997 |
| WO | WO 98/17627 A1 | 4/1998 |
| WO | WO 99/08671 A1 | 2/1999 |
| WO | WO 99/12537 A1 | 3/1999 |
| WO | WO 99/21824 A1 | 5/1999 |
| WO | WO 99/31057 A1 | 6/1999 |
| WO | WO 99/31074 A2 | 6/1999 |
| WO | WO 99/31075 A1 | 6/1999 |
| WO | WO 99/31074 A3 | 11/1999 |
| WO | WO 99/61424 A1 | 12/1999 |
| WO | WO 00/15511 A1 | 3/2000 |
| WO | WO 00/31020 A1 | 6/2000 |
| WO | WO 00/50027 A1 | 8/2000 |
| WO | WO 00/53225 A1 | 9/2000 |
| WO | WO 02/00209 A2 | 1/2002 |
| WO | WO 02/00209 A3 | 1/2003 |
| WO | WO 03104184 A1 * | 12/2003 |
| WO | WO 2005/092318 A1 | 10/2005 |
| WO | WO 2005/092392 A2 | 10/2005 |
| WO | WO 2005/102390 A2 | 11/2005 |
| WO | WO 2005/102390 A3 | 5/2006 |
| WO | WO 2005/092392 A3 | 10/2006 |
| WO | WO 2006/113568 A2 | 10/2006 |
| WO | WO 2006/113568 A3 | 4/2007 |
| WO | WO 2007/038620 A2 | 4/2007 |
| WO | WO 2007/052999 A1 | 5/2007 |
| WO | WO 2007/090661 A2 | 8/2007 |
| WO | WO 2007/090661 A3 | 9/2007 |
| WO | WO 2007/038620 A3 | 10/2007 |
| WO | WO 2008/009663 A1 | 1/2008 |
| WO | WO 2008/010222 A2 | 1/2008 |
| WO | WO 2008/011016 A2 | 1/2008 |
| WO | WO 2008/010222 A3 | 4/2008 |

(Continued)

OTHER PUBLICATIONS

Morrison et. al., Morrison and Boyd: Organic Chemistry, 1992, Prentice Hall, 6th ed., pp. 770-771 and p. 778.*
Bamba et al. Release mechanisms in gelforming sustained release preparations. International Journal of Pharmaceutics. 1979;2:307-315.
Bangham et al. Diffusion of univalent ions across the lamellae of swollen phospholipids. J. Mol. Biol. 1965;13:238-252.
Berger et al. Change in opioid use after the initiation of gabapentin therapy in patients with postherpetic neuralgia. Clinical Therapeutics. 2003;25(11):2809-2821.
Chavanpatil et al. Novel sustained release, swellable and bioadhesive gastroretentive drug delivery system for olfoxacin. International Journal of Pharmaceutics. 2006;316(1-2):86-92.

(Continued)

*Primary Examiner* — Sreeni Padmanabhan
*Assistant Examiner* — Sarah Pihonak
(74) *Attorney, Agent, or Firm* — Wilson Sonsini Goodrich & Rosati

(57) ABSTRACT

In one aspect, the present invention provides a composition of a covalent conjugate of a GABA analog with a drug. In another aspect, the present invention provides methods for treating pain and neurological disorders using the conjugates of GABA analogs.

13 Claims, No Drawings

FOREIGN PATENT DOCUMENTS

WO    WO 2008/011016 A3    8/2008

OTHER PUBLICATIONS

Codd et al. Tramadol and several anticonvulsants synergize in attenuating nerve injury-induced allodynia. Pain. 2008;134:254-262.

Dimitrijevic et al. Drosophila $GABA_B$ receptors are involved in behavioral effects of γ-hydroxybutyric acid (GHB). Eur. J. Pharmacol. 2005;519(3):246-52.

Durmus et al. The post-operative analgesic effects of a combination of gabapentin and paracetamol in patients undergoing abdominal hysterectomy: a randomized clinical trial. Acta Anaesthesiol Scand. 2007;51:299-304.

Eckhardt et al. Gabapentin Enhances the Analgesic Effect of Morphine in Healthy Volunteers. Anesth Analg. 2000;91:185-191.

Hoffman et al. Pharmacokinetic and pharmacodynamic aspects of gastroretentive dosage forms. Int. J. Pharm. 2004;11:141-53.

Hurley et al. Gabapentin and Pregabalin Can Interact Synergistically with Naproxen to Produce Antihyperalgesia. Anesthesiology. 2002;97(5):1263-1273.

International search report dated Apr. 27, 2010 for PCT Application No. US2009/60058.

Jain, K.K. Strategies and technologies for drug delivery systems. TiPS. 1998;19:155-157.

Jezyk et al. Transport of Pregabalin in Rat Intestine and Caco-2 Monolayers. Pharm. Res. 1999;16:519-526.

Kazi et al. Gabapentin completely attenuated the acute morphine induced c-Fos expression in the rat striatum. Mol. Neurosci. 2007;32:47-52.

Keskinbora et al. Gabapentin and an Opioid Combination Versus Opioid Alone for the Management of Neuropathic Cancer Pain: A Randomized Open Trial. J. of Pain and Symptom Management. 2007;34(2):183-189.

Klausner et al. Novel gastroretentive dosage forms: evaluation of gastroretentivity and its effect on levodopa in humans. Pharm. Res. 2003;20:1466-73.

Rose et al. Gabapentin: pharmacology and its use in pain management. Anesthesia. 2002;57(5):451-462.

Saudek et al. A preliminary trial of the programmable implantable medication system for insulin delivery. N. Engl. J. Med. 1989;321:574-579. Abstract only.

Stewart et al. Comparison of intestinal permeabilities determined in multiple in vitro and in situ models: relationship to absorption in humans. Pharm. Res. 1995;12:693-699.

Streubel et al. Gastroretentive drug delivery systems. Expert Opin. Drug Deliver. 2006;3:217-3.

Szoka et al. Procedure for preparation of liposomes with large internal aqueous space and high capture by reverse-phase evaporation. PNAS. 1978;75:4194-4198.

Tiippana et al. Do surgical patients benefit from perioperative gabapentin/pregabalin? A systematic review of efficacy and safety. Anesthesia & Analgesia. 2007;104(6):1545-1556.

Verma et al. Osmotically controlled oral drug delivery. Drug Dev. Ind. Pharm., 2000;26:695-708.

Wu et al. Gamma-hydroxybutyric acid (GHB) and gamma-aminobutyric acidB receptor (GABABR) binding sites are distinctive from one another: molecular evidence. Neuropharmacology. 2004;47(8):1146-56.

Yoon et al. Evaluation of interaction between gabapentin and ibuprofen on the formalin test in rats. Anesthesiology. 1999;91(4):1006-1013.

European search report and opinion dated Mar. 27, 2012 for EP Application No. 09819911.0.

Shi, et al. Design, synthesis, and preliminary evaluation of gabapentin-pregabalin mutual prodrugs in relieving neuropathic pain. Arch Pharm (Weinheim). Aug. 2005;338(8):358-64.

* cited by examiner

DRUG CONJUGATES AND METHODS OF USE THEREOF

CROSS-REFERENCE

This application claims the benefit of U.S. Provisional Application No. 61/103,800, filed Oct. 8, 2008, which application is incorporated herein by reference.

BACKGROUND OF THE INVENTION

A number of treatments involving the administration of single drugs are currently recommended for relief of pain including neurological pain. The single administration of narcotic analgesics, gamma (γ)-aminobutyric acid (GABA) analogs such as gabapentin, pregabalin and baclofen, antidepressants and non-steroidal anti-inflammatory drugs (NSAIDs) have been shown to display pain alleviating properties in the clinic and in various animal models.

Despite the benefits derived from the current single drug pain relief regimens, these regimens have disadvantages. One area of concern relates to the incidence of unwanted side effects caused by many of the pain treatment regimens available today. Narcotic analgesics, such as morphine, are sparingly prescribed for chronic pain because of the well-known addictive effects and central nervous system (CNS) side effects and gastrointestinal side effects resulting from their single administration.

Another concern of the current pain treatment regimens relates to their effectiveness. Many single active ingredients such as antidepressant agents or GABA analogs employed in current pain relief regimens cannot achieve adequate pain alleviation even at their maximum approved therapeutic doses in certain severe pain states. In addition to not achieving adequate pain alleviation, increasing the drug dose may produce an increase in unwanted side effects such as cognitive impairment, nausea, and constipation.

Furthermore, other concerns of GABA analogs and many narcotic analgesics relate to their less favorable pharmacokinetic and physiological properties. Many orally administrated opioid molecules are extensively metabolized by digestive organs before reaching systemic circulation. Rapid systemic clearance and saturable absorption of some of the GABA analogs have limited these drugs to reach their full potential in treatment of pain and other CNS disorders. These sub-optimal properties often lead to less than adequate efficacy and unwanted side effects in patients.

Sustained released formulations are a conventional method to address the issue of rapid systemic clearance, as it is well known to those skilled in the art (e.g., "Remingtion's Pharmaceutical Sciences," Philadelphia College of Pharmacy and Science, 17$^{th}$ Edition, 1985). GABA analogs, such as baclofen, gabapentin and pregabalin are not absorbed through the large intestine. Rather, these compounds are typically absorbed in the small intestine by the neutral amino transporter systems (Jezyk et al., Pharm. Res., 1999, 16, 519-526). The rapid passage of conventional tract has prevented the successful application of sustained release approach to these GABA analogs.

In view of these concerns, it is evident that there is a need for an improved pain regimen that provides an improved therapeutic benefit (i.e., reduced severity and/or frequency of pain) and/or reduces the incidence of unwanted side effects caused by many of the current regimens. In addition, improving pharmacokinetic profile of GABA analogs will also lead to more customized dosing regimens according to patients' need.

SUMMARY OF THE INVENTION

In one aspect, the present invention provides a compound comprising a first moiety and a second moiety, the first moiety being covalently linked via an amino terminus or an acidic terminus other than a carboxylic acid group to the second moiety, wherein the first moiety is γ-aminobytyric acid (GABA) or an analog or derivative of GABA. In another aspect, the present invention provides a compound comprising a first moiety and a second moiety, the first moiety being covalently linked via a carboxylic acid group to the second moiety, and an amino terminus of the first moiety is linked to a protection group, wherein the first moiety is GABA or an analog or derivative of GABA. The present invention also embodies a pharmaceutical composition comprising the compound of the invention disclosed herein and a pharmaceutically acceptable carrier.

In another aspect, the present invention provides a method of preventing or treating a disorder, the method comprising administering to a subject in need thereof a therapeutically effective amount of a compound of the invention. In some embodiments, the compound used in the method of treatment comprises a first moiety and a second moiety, the first moiety being covalently linked via an amino terminus or an acidic terminus other than a carboxylic acid group to the second moiety, wherein the first moiety is GABA or an analog or derivative of GABA. In other embodiments, the compound used in the method of treatment comprises a first moiety and a second moiety, the first moiety being covalently linked via a carboxylic acid group to the second moiety, and an amino terminus of the first moiety is linked to a protection group, wherein the first moiety is GABA or an analog or derivative of GABA. In still other embodiments, the method comprises administering to a subject in need thereof a therapeutically effective amount of a pharmaceutical composition of the invention. Such pharmaceutical composition comprises the compound of the invention and a pharmaceutically acceptable carrier.

In yet another aspect, the present invention provides a method for reducing an adverse effect associated with a treatment of a disorder, the method comprising administering to a subject in need thereof a therapeutically effective amount of a compound of the invention. In some embodiments, the compound comprises a first moiety and a second moiety, the first moiety being covalently linked via an amino terminus or an acidic terminus other than a carboxylic acid group to the second moiety, wherein the first moiety is GABA or an analog or derivative of GABA. In other embodiments, the compound comprises a first moiety and a second moiety, the first moiety being covalently linked via a carboxylic acid group to the second moiety, and an amino terminus of the first moiety is linked to a protection group, wherein the first moiety is GABA or an analog or derivative of GABA. In still other embodiments, the method for reducing an adverse effect associated with a treatment of a disorder comprises administering to a subject in need thereof a therapeutically effective amount of a pharmaceutical composition of the invention. Such pharmaceutical composition comprises the compound of the invention and a pharmaceutically acceptable carrier.

In still another aspect, the present invention provides a method for enhancing the therapeutic efficacy of a treatment of a disorder, the method comprising administering to a subject in need thereof a therapeutically effective amount of a compound of the invention. In some embodiments, the compound comprises a first moiety and a second moiety, the first moiety being covalently linked via an amino terminus or an acidic terminus other than a carboxylic acid group to the second moiety, wherein the first moiety is GABA or an analog or derivative of GABA. In other embodiments, the compound comprises a first moiety and a second moiety, the first moiety being covalently linked via a carboxylic acid group to the second moiety, and an amino terminus of the first moiety is linked to a protection group, wherein the first moiety is GABA or an analog or derivative of GABA. In still other embodiments, the method for enhancing the therapeutic efficacy of a treatment of a disorder comprises administering to a subject in need thereof a therapeutically effective amount of a pharmaceutical composition of the invention. Such pharmaceutical composition comprises the compound of the invention and a pharmaceutically acceptable carrier.

In practicing some aspects of the inventions disclosed herein, the first moiety of the compound is a GABA analog. In some embodiments, the first moiety is a baclofen, vigabatrin, gabapentin, or pregabalin, or a γ-amino-phosphinic acid derivative. In some embodiments, the second moiety is an analgesic drug, including but not limited to, a nonsteroidal anti-inflammatory drug (NSAID), an opioid, an anesthetics, a muscle relaxant, or an anti-depressant. In other embodiments, the second moiety is a γ-hydroxybutyric acid (GHB), or an analog, derivative, or variant of GHB. The first and second moieties are preferably linked via a covalent bond. Such covalent bond may be an ester bond, an amide bond, an imine bond, a carbamate bond, a carbonate bond, a thioester bond, an acyloxycarbamate bond, an acyloxycarbonate bond, a phosphate bond, an acyloxyphosphate bond or mono-, di-alkylphosphoramidate bond. In some embodiments, the invention further comprises a linker that covalently links the first moiety to the second moiety. Such linker is preferably physiologically labile. In some embodiments, the invention further comprises a third moiety that is ionically or covalently linked to the first moiety or second moiety of the compound. In other embodiments, the compound can be used in combination with at least one other therapeutic agent, which may be an anti-psychotic drug, an anxiolytic drug, an anti-depressant drug, an anti-convulsive drug, an antiparkinsonian drug, an acetylcholine esterase inhibitor, a MAO inhibitor, a selective serotonin reuptake inhibitor (S SRI), an N-methyl-D-aspartic acid (NMDA) antagonist, or a selective noradrenalin replace inhibitor. Such other therapeutic agent may be administered prior to, concomitant with or subsequent to administering the compound of the present invention. In some embodiments, the present invention also provides a protection group linked to the amino terminus of the first moiety, e.g. a GABA analog. The protection group may be an amino acid, an imine, a carbamate, an N-dithiasuccinimide, a mono- or di-alkylphosphoramidate, or an acyloxycarbamate. Preferably, the protection group is cleavable from the amino group of the first moiety following administration to a subject.

The present invention also provides methods for use in the treatment of a disorder, for reducing side effects induced by the compound of the invention, and for enhancing the therapeutic efficacy of the compound of the invention. In practicing any of the subject methods disclosed herein, preferably the disorder being treated is a pain or a neurological disorder. In some embodiments, the pain is an acute, chronic, or inflammatory pain. In other embodiments, the neurological disorder is an anxiety disorder, a depression, a dissociative disorder, a personality disorder, a cognitive disorder, a mood disorder, an affective disorder, a neurodegenerative disorder, a convulsive disorder, Parkinson's disease, Alzheimer's disease, epilepsy, schizophrenia, paranoia, psychosis, Huntington's disease, Gilles de la Tourette's syndrome, faintness attacks, hypokinesia, cranial disorders, neurodegenerative disorders, panic, insomnia, addictive disorders, or a restless leg syndrome. In certain embodiments, the subject is an animal, preferably a mammal, more preferably a human. In some embodiments, administering the compound or the pharmaceutical composition of the invention results in at least one less side effect as compared to administering the individual moiety alone. In other embodiments, administering the compound or the pharmaceutical composition of the invention results in enhanced therapeutic activity as compared to administering the individual moiety alone. In certain embodiments, the compound or the pharmaceutical composition is administered in combination with another agent. Such other agent can be administered prior to, concomitant with, or subsequent to administering the compound or the pharmaceutical composition of the invention.

Further provided in the present invention is a kit for preventing or treating pain or a neurological disorder in a subject, the kit comprising a compound of the invention or a pharmaceutical composition of a compound of the invention, and instructions for using the kit. In some embodiments, the subject is an animal, preferably a human. In other embodiments, the kit further comprises at least one other agent for use in the treatment of pain or a neurological disorder, for reducing side effects induced by the compound of the invention, and/or for enhancing the therapeutic efficacy of the compound of the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

In one aspect, the invention provides a GABA-Drug conjugate comprising at least two moieties that are linked through a covalent bond. The first moiety of the conjugate preferably comprises a GABA analog. In some embodiments, the second moiety of the conjugate comprises an analgesic drug. In other embodiments, the second moiety of the conjugate comprises gamma (γ)-hydroxybutyric acid (GHB). The analgesics of the second moiety of the conjugate can include, but are not limited to, narcotics, NSAIDs, antidepressants, anesthetics, muscle relaxants, gamma-hydroxybutyric acid, dual-acting opioids agonists, N-methyl-D-aspartic acid (NMDA) receptor antagonists, and any pharmaceutical composition of the drugs mentioned herein. The present invention also provides methods for synthesizing and producing these GABA-Drug conjugates. Further, the present invention includes methods for using the GABA-Drug conjugates of the invention and pharmaceutical composition of the GABA-Drug conjugates for treating and/or preventing disorders.

The present invention of GABA-Drug conjugates preferably provides pharmaceutical advantages of use in medicine. First, these GABA-Drug conjugates are labile in vivo, cleaved by either enzymatic or chemical pathway to generate substantial quantities of a GABA analog and a drug e.g. an analgesic selected from narcotics, NSAIDs, antidepressants, dual-acting opioids, anesthetics, muscle relaxants, and gamma-hydroxybutyric acid upon reaching the systemic circulation. Second, each individual moiety of the GABA-Drug conjugate, upon cleavage in vivo, targets a different or non-overlapping biological target that is relevant for the treatment sought, for example, treatment for pain or neurological disorder. Thus, the GABA-Drug conjugate, upon cleavage in vivo, is able to target more than one biological target and elicit additive or synergistic biological effects, resulting in enhanced therapeutic efficacy. The linkers released from the GABA-Drug conjugate are generally non-toxic when administered to a subject with an appropriate dosing regimen.

Examples of an acidic group include, but are not limited to, phosphic acid, phosphonic acid, sulfonic acid, sulfinic acid or carboxylic acid; and the like. An amino terminus is also known as the N-terminus, $NH_2$-terminus, N-terminal end or amine-terminus. These terms are used interchangeably herein. Amino terminus includes the end of a protein or polypeptide terminated by an amino acid with a free amine group (—$NH_2$). A bridged cycloalkyl includes a radical comprising

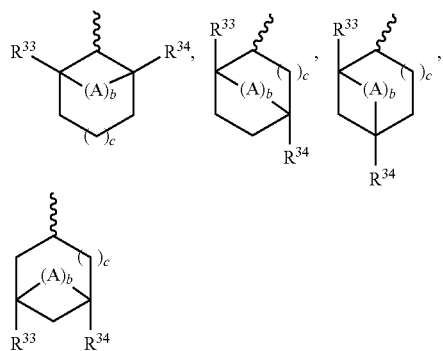

wherein:

A is $(CR^{35}R^{36})_b$;

$R^{35}$ and $R^{36}$ are independently selected from the group consisting of hydrogen and methyl;

$R^{33}$ and $R^{34}$ are independently selected from the group consisting of hydrogen and methyl;

b is an integer from 1 to 4; and c is an integer from 0 to 2.

Examples of GABA analogs include but are not limited to the following structures:

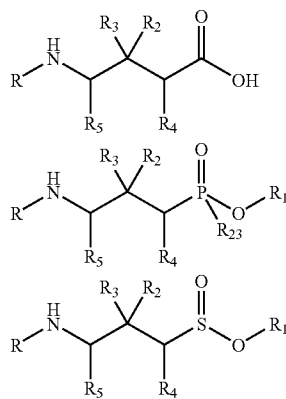

wherein:

R is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or R and $R_4$ together with the atoms to which they are attached form an azetidine, substituted azetidine, pyrrolidine or substituted pyrrolidine ring;

$R_4$ and $R_5$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl; and $R_2$ and $R_3$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl and bridged cycloalkyl ring.

$R_1$ and $R_{23}$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalky.

The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including but not limited to the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including but not limited to the enol form, the keto form and mixtures thereof. Accordingly, the chemical structures depicted herein encompass all possible tautomeric forms of the illustrated compounds. The compounds of the invention also include, but are not limited to, isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$. Further, it should be understood, when partial structures of the compounds of the invention are illustrated, that brackets indicate the point of attachment of the partial structure to the rest of the molecule.

In one aspect, the second moiety of the invention, for example, a drug, is typically attached to the gamma-amino group of the first moiety, e.g. a GABA analog. The two moieties may be directly attached through the gamma-amino group of a GABA analog to form the following linkers including, but not limited to, carboxylic amide, phosphonic amide, phosphinic amide, sulphonic amide, sulphinic amide, and imine, or may optionally be linked through a linker "X" which may be cleaved in vivo. In another aspect, the second moiety of the invention is attached to the first moiety, for example, a GABA analog, via the acidic group of the first moiety. The acidic group as used herein includes, but is not limited to, carboxylic acid, phosphic acid and sulfinic acid group. The second moiety of the conjugate is covalently linked to the acidic group of the first moiety to form the following linkers including but not limited to carboxylate, thio-esters, phosphinate, sulfinate, and carboxylic amide. Alternatively, the two moieties may optionally be linked through a linker "Z" that may be cleaved in vivo.

In some embodiments, the present invention provides the GABA-Drug conjugate of Formulas (I) and (II):

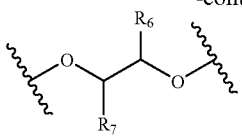

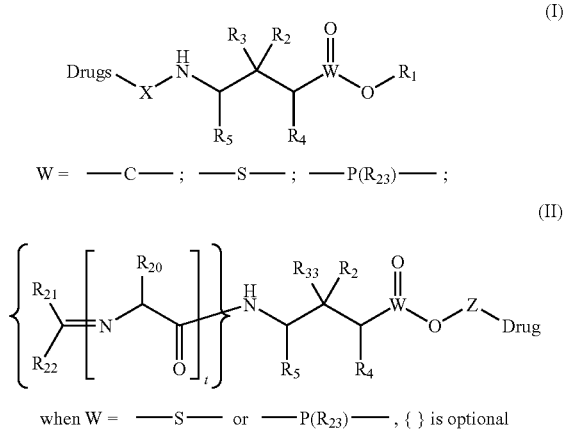

or a pharmaceutically acceptable salt, hydrate, solvate and isotope, wherein:

t is 0 or 1;

X is defined as a covalent bond via a linker between a drug and a GABA analog that is selected from the group consisting of the following:

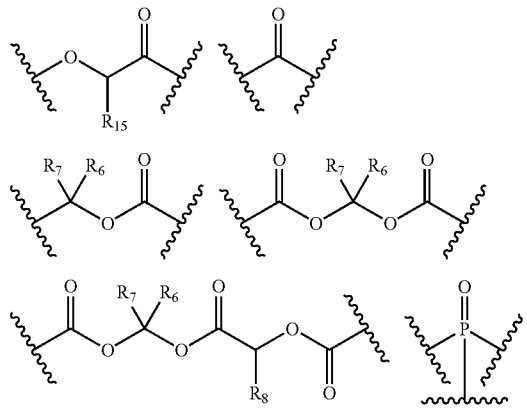

Z is defined as a covalent bond via a linker between a drug and a GABA analog that is selected from the group consisting of the following:

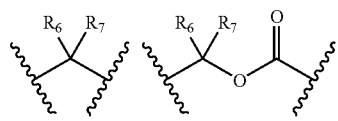

$R_1$ is independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteraryl, substituted heteroaryl, heteroarylalkyl and substituted heteroarylalkyl;

$R_2$ and $R_3$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted arylalkyl, heteroarylalkyl and substituted heteroarylalkyl or optionally, $R_2$ and $R_3$ together with the carbon atom to which they are attached form a cycloalkyl, substituted cycloalkyl, cycloheteroalkyl, substituted cyclohetereoalkyl or bridged cycloalkyl ring;

$R_4$ and $R_5$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R_6$ and $R_7$ are independently selected from the group consisting of hydrogen, alkyl, substituted alkyl, acyl, substituted alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, arylalkyl, substituted arylalkyl, heteroarylalkyl and substituted heteroarylalkyl or optionally, $R_4$ and $R_5$ together with the carbon atom to which they are attached form a cycloalkyl, substituted cycloalkyl, cycloheteroalkyl, substituted cyclohetereoalkyl or bridged cycloalkyl ring;

$R_{20}$ is independently selected from the group consisting of hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy, or optionally;

$R_{21}$ and $R_{22}$ are independently selected from the group consisting of hydrogen, acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl or optionally $R_{20}$ and $R_{21}$ together with the carbon atom to which they are attached form a cycloalkyl, substituted cycloalkyl, cycloheteroalkyl or substituted cycloheteroalkyl ring.

In another aspect, the second moiety of the invention is attached to the first moiety, for example, a GABA analog, via the C (carboxyl)-terminus of the first moiety, and the N (amino) terminus of the first moiety is attached to a protection group "P". In some embodiments, the GABA-Drug conjugate of the present invention has the Formula (III)

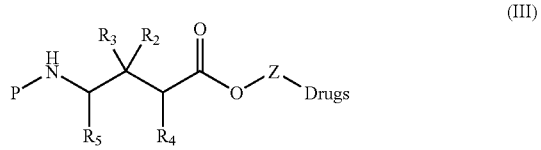

(III)

wherein

R₂ and R₃ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted arylalkyl, heteroarylalkyl and substituted heteroarylalkyl or optionally, R₂ and R₃ together with the carbon atom to which they are attached form a cycloalkyl, substituted cycloalkyl, cycloheteroalkyl, substituted cyclohetereoalkyl and bridged cycloalkyl ring;

R₄ and R₅ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

Z is defined as a covalent bond via a linker between a drug and a GABA analog that is selected from the group consisting of the following:

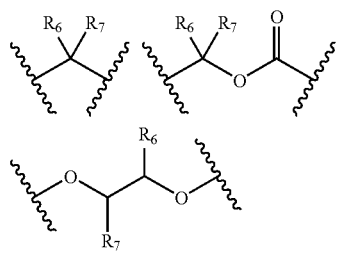

P is defined as an amino acid, an imine, a carbamate, an N-dithiasuccinimide, a mono- or di-alkyl phosphoramidate, acyloxycarbamate.

I. First Moiety: GABA and GABA Analogs

In one aspect, the present invention provides a composition for treating pain or a neurological disorder. In some embodiments, the first moiety of the composition is a GABA analog.

Gamma-aminobutyric acid (GABA) is one of the inhibitory neurotransmitters in the central nervous system of mammals. It acts at inhibitory synapses in the brain by binding to specific transmembrane receptors in the plasma membrane of both pre- and postsynaptic neuronal processes. This binding causes the opening of ion channels to allow the flow of either negatively charged chloride ions into the cell or positively charged potassium ions out of the cell. This action results in a negative change in the transmembrane potential, usually resulting in hyper-polarization. Three general GABA receptors have been identified, $GABA_A$, $GABA_B$ and $GABA_C$. $GABA_A$ and $GABA_C$ are ionotropic receptors, whereas $GABA_B$ is a G protein coupled metabotropic receptor. Low levels of GABA have been linked to many diseases including but not limited to epileptic seizures, multiple sclerosis, action tremors, panic, anxiety, and depression.

The role that GABA plays in various disease states has stimulated interests in preparing GABA analogs that have better pharmaceutical properties as compared to GABA, which lacks blood brain barrier penetration. Accordingly, a number of GABA analogs have been synthesized in the art (Satzinger et al., U.S. Pat. No. 4,04,175; Silverman et al., U.S. Pat. Nos. 5,563,175; 6,028,214; 6,117,906; International Publication No. WO92/09560; 93/23383; Horwell et al., U.S. Pat. No. 6,020,370; International Publication No. WO97/29101, 97/33858; 97/33859; Bryans et al., International Publication No. WO 99/31057; 99/31075; 99/61424; 00/15511; 00/31020; 00/50027; 02/00209; Guglietta et al. International Publication No. WO 99/08671).

A number of GABA analogs have been identified. These GABA analogs include but are not limited to baclofen [Formula IV (a)], vigabatrin [Formula IV (b)], gabapentin [Formula IV (c)], and pregabalin [Formula IV (d)] as shown below. Unlike GABA itself, these GABA derivatives not only can pass through the blood-brain barrier likely by active transport mechanism, but also demonstrate pharmaceutical utilities clinically. Baclofen is a $GABA_B$ agonist that is clinically used for the treatment of spastic movement or relief of pain, especially in instances of spinal cord injury, spastic diplegia, multiple sclerosis and trigeminal neuralgia. Vigabatrin is an anti-convulsant that has been used as an adjunctive treatment for diseases such as epilepsy and complex partial seizures. Among GABA analogs, gabapentin and pregabalin were originally developed for the treatment of epilepsy, but have been proven to be effective to relieve chronic pain, especially neuropathic pain such as diabetic neuropathic pain and postherpetic neuralgia. Gabapentin and pregabalin have also shown effectiveness in fibromyalgia treatment. Gabapentin and pregabalin are in general well tolerated in most patients, have relatively mild side effect profile, minimum metabolism and drug-drug interaction. Gabapentin and pregabalin seem to have minimum interaction with GABA receptors. Studies suggest that the neuropathic pain alleviation action is mediated through alpha-2-delta subunit of the voltage-gated N-type calcium ion channel, a high affinity binding site in neuronal membranes (Rose, M. A. et al, *Anesthesia*, 2002, 57(5), 451-462). This subunit has been implicated in the maintenance of mechanical hypersensitivity in models of neuropathic pain. Calcium ions enable vesicles containing neurotransmitters to fuse with the presynaptic membrane, an action that promotes the release of neurotransmitters that inhibit the synaptic cleft. Both gabapentin and pregabalin probably exert their therapeutic effects by blocking calcium influx via alpha-2-delta receptor and reducing the release of neurotransmitters that transmit nociceptive signals between neurons. In vitro findings suggest that gabapentin may reduce presynaptic release of excitatory neurotransmitters such as glutamate and norepinephrine.

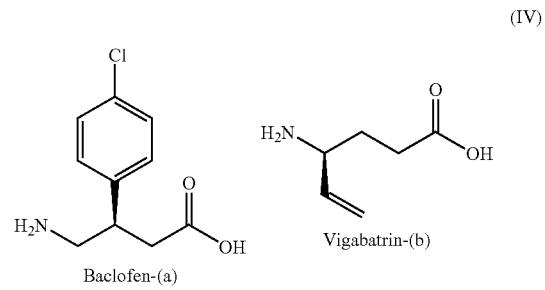

(IV)

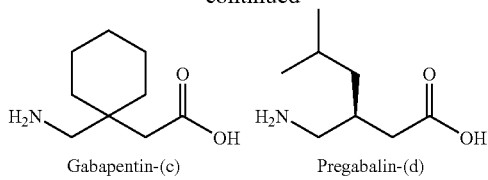

Gabapentin-(c)    Pregabalin-(d)

Combination therapy using GABA analogs (e.g. gabapentin, pregabalin and baclofen) with other analgesics such as narcotics, dual-acting opioids analgesics, NSAIDs, antidepressants, NMDA antagonists results in improvement in chronic pain control. When administered together, GABA analogs and these analgesics can interact in a synergistic or additive manner to control chronic pain. This synergy can potentially allow a reduction in the dose required of each compound, leading to a reduction in the side effects, and enhancement of the clinical utility of these compounds. The analgesic effects can be enhanced by co-administration of GABA analogs (gabapentine, pregabalin and baclofen) together with opioids such as morphine (Keskinbora K. J. of Pain and Symptom Management 2007, 34(2), 183-189; Kazi, J. A., Gee, C. F. J. Mol. Neurosci. 2007, 32, 47-52; Berger, A.; et al. Clinical Therapeutics 2003, 25(11), 2809-2821; Eckhardt, K. et al. Anesth Analg 2000, 91, 185-191; Granados-Soto, V. et al. Pharmacology 2005, 74, 200-208; Tiippana, E. M.; et al. Anesthesia & Analgesia 2007, 104(6), 1545-1556; Codd. E. E.; et al. Pain 2008, 134, 254-262.). It has also been reported in accordance with the present invention that analgesic effects can be enhanced by the co-administration of GABA analogs (gabapentin, pregabalin) together with NSAIDs or NMDA receptor antagonists (Yoon, M. H. et al., Anesthesiology 1999, 91(4), 1006-1013; Hurley, R. W., et al., 2002, 97(5), 1263-1273; Durmus, M. et al., Acta Anaesthesiol Scand 2007, 51, 299-304; Ryan, M. et al., International Patent No. WO99/12537).

Despite the benefit of using co-administration of GABA analogs and other analgesics, these regimens have disadvantages: 1) rapid systemic clearance of GABA analogs including but not limited to gabapentin, pregabalin and baclofen, which consequently requires frequent dosing to maintain a therapeutic or prophylactic concentration in the systemic circulation; 2) inter-patient variability due to the saturation of absorption of gabapentin at higher doses (1.8-3.6 g/d in divided doses); 3) minimum absorption in large intestine which limits the sustained released formulation solution; 4) GI toxicity caused by analgesics, e.g. NSAIDs; and 5) extensive first pass metabolism for some of the narcotic analgesics such as morphine.

In one aspect, the present invention provides a novel GABA-drug conjugate which has a new chemical entity that preferably has several distinct advantages over the above mentioned treatment regimens. In some embodiments, the GABA-drug conjugate may be absorbed in large intestine. As a result, the dosing frequency can be reduced by using sustained release formulations. In other embodiments, the GABA-Drug conjugate alters the absorption mechanism of GABA analogs, likely through passive diffusion, and may provide more predictive pharmacokinetic and therapeutic outcome among patients. In further embodiments, by optimizing the linker between the first moiety, e.g. a GABA analog, and the second moiety, e.g. an analgesic, the rate of release of the active drugs (i.e. the active form of GABA analog and the active form of the analgesic) from the GABA-drug conjugate can be optimized. As a result, some of the GI liability such as the first pass metabolism or GI side effects may be reduced as compared to dosing of the parent drugs. The present invention also encompasses a GABA-analgesic conjugate, for example, a GABA-NSAID conjugate. Administering the GABA-NSAID conjugate of the present invention may potentially prevent, reduce, and/or treat gastrointestinal damages caused by NSAID.

II. Second Moiety

In some embodiments, the second moiety of the composition of the present invention is an analgesic drug.

A. Analgesics

An analgesic is any member of the group of drugs used to relieve pain. Analgesic drugs act in various ways in the peripheral and central nervous systems. There are several classes of analgesics, which include, but are not limited to, paracetamol (acetaminophen), the non-steroidal anti-inflammatory drugs (NSAIDs) such as the Naproxen, narcotic drugs such as morphine and opiates, synthetic drugs with narcotic properties such as tramadol, and various others.

The choice of analgesia is determined by the severity and response to other medication, and is also determined by the type of pain. For example, for neuropathic pain, traditional analgesia is less effective, and there is often benefit from classes of drugs that are not normally considered analgesics, such as tricyclic antidepressants and anticonvulsants.

Non-Steroidal Anti-Inflammatory Drugs (NSAIDs)

Non-steroidal anti-inflammatory drugs (NSAIDs or NAIDs), sometimes also referred to as non-steroidal anti-inflammatory agents/analgesics (NSAIAs) or non-steroidal anti-inflammatory medicines (NSAIMs), are drugs with analgesic, antipyretic and, in higher doses, anti-inflammatory effects. NSAIDs can reduce pain, fever and inflammation. The term "non-steroidal" is used to distinguish these drugs from steroids, which have a similar cicosanoid-depressing, anti-inflammatory effect. As analgesics, NSAIDs are non-narcotic. NSAIDs include but are not limited to diclofenac, etodolac, indomethacin, sulindac, tolmetin, nabumetone, piroxicam, acetaminophen, fenoprofen, flurbiprofen, ibuprofen, ketoprofen, naproxen, oxaprozin, aspirin, choline magnesium trisalicylate, diflunisal, meclofenamic acid, mefenamic acid, phenylbutazone, fluocinolone acetonide, prednisolone, prednisolone tertiary-butylacetate, dexamethasone, or prodrugs or active metabolites thereof. The most prominent members of this group of drugs are aspirin, ibuprofen, and naproxen. Paracetamol (acetaminophen) has negligible anti-inflammatory activity, and is not an NSAID.

Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid. Prostaglandins act as messengers in the process of inflammation. NSAIDs are usually indicated for the treatment of acute or chronic conditions where pain and inflammation are present. COX2 inhibitors include but are not limited to rofecoxib (VIOXX™, or 4-[4-(methylsulfonyl)phenyl]-3-phenyl-2(5H)-furanone), celecoxib (CELEBREX™, or 4-[5-(4-methylphenyl)-3-(trifluoromethyl)-1H-pyrazol-1-yl]benzenesulfonamide), and valdecoxib (BEXTRA™, and 4-(5-methyl-3-phenyl-4-isoxazolyl)benzenesulfonamide).

NSAIDs are generally indicated for the symptomatic relief of conditions including but not limited to rheumatoid arthritis, osteoarthritis, inflammatory arthropathies, acute gout, dysmenorrhoea, metastatic bone pain, headache and migraine, postoperative pain, mild-to-moderate pain due to inflammation and tissue injury, pyrexia (fever), ileus, and renal colic.

The two main adverse drug reactions (ADRs) associated with NSAIDs relate to gastrointestinal (GI) effects and renal effects of the agents. These effects are dose-dependent, and in many cases severe enough to pose the risk of ulcer perforation, upper gastrointestinal bleeding, and death, limiting the use of NSAID therapy. An estimated 10-20% of NSAID patients experience dyspepsia, and NSAID-associated upper gastrointestinal adverse events are estimated to result in 103,000 hospitalizations and 16,500 deaths per year in the United States, and represent 43% of drug-related emergency visits.

In some aspects, the present invention provides a composition that may reduce the side effects associated with the traditional analgesics and increase the therapeutic efficacy of the treatment.

Narcotic Analgesics

There are two types of narcotic analgesics: the opiates and the opioids (derivatives of opiates). Opiates are the alkaloids found in opium including but not limited to morphine, codeine and thebaine. Opioids are any medication which bind to opioid receptors in the central nervous system or gastointestinal tract. There are four broad classes of opioids: endogenous opioid peptides (produced in the body: endorphins, dynorphins, enkephalins); opium alkaloids (morphine, codeine, thebaine); semi-synthetic opioids (heroin, oxycodone, hydrocodone, dihydrocodeine, hydromorphone, oxymorphone, nicomorphine); and fully synthetic opioids (pethidine or Demerol, methadone, fentanyl, propoxyphene, pentazocine, buprenorphine, butorphanol, tramadol, and more).

Opioids are used in medicine as strong analgesics, for relief of severe or chronic pain. There is no upper limit for the dosage of opioids used to achieve pain relief, but the dose must be increased gradually to allow for the development of tolerance to adverse effects (for example, respiratory depression). There have been debates over the addictive potential of opioids vs. the benefit of their analgesic properties for treating non-malignant chronic pain, such as chronic arthritis. There are many side effects and adverse reactions associated with usage of narcotic analgesics. The common side effects include but are not limited to nausea, vomiting, drowsiness, dry mouth, miosis (contraction of the pupil), orthostatic hypotension, urinary retention, constipation and/or fecal impaction.

Psychotropic Agents

Tetrahydrocannabinol (THC) and some other cannabinoids, either from the *Cannabis sativa* plant or synthetic, have analgesic properties. Other psychotropic analgesic agents include but are not limited to ketamine (an NMDA receptor antagonist), clonidine and other $\alpha_2$-adrenoreceptor agonists, mexiletine and other local anesthetic analogues.

Atypical and/or Adjuvant Analgesics

Orphenadrine, cyclobenzaprine, scopolamine, atropine, gabapentin, first-generation antidepressants and other drugs possessing anticholinergic and/or antispasmodic properties are used in many cases along with analgesics to potentiate centrally acting analgesics such as opioids when used against pain especially of neuropathic origin and to modulate the effects of many other types of analgesics by action in the parasympathetic nervous system. Tricyclic antidepressants, especially amitriptyline, have been shown to improve pain. The exact mechanism of carbamazepine, gabapentin and pregabalin is unclear, but these anticonvulsants are used to treat neuropathic pain with modest success. Dextromethorphan has been noted to slow the development of tolerance to opioids and exert additional analgesia by acting upon the NMDA receptors; some analgesics such as methadone and ketobemidone and perhaps piritramide have intrinsic NMDA action.

Strong liquor has been used in the past as an agent for dulling pain, due to the CNS depressant effects of ethyl alcohol. However, the ability of alcohol to treat pain is inferior to virtually all analgesics used today (e.g. morphine, codeine).

The use of adjuvant analgesics is a growing part of the pain-control field. Many of these drugs combat the side effects of opioid analgesics. For example, antihistamines including orphenadrine combat the release of histamine caused by many opioids, methylphenidate, caffeine, ephedrine, dextroamphetamine, and cocaine work against heavy sedation and may elevate mood in distressed patients as do the antidepressants. A well-accepted benefit of THC to chronic pain patients on opioids is its superior anti-nauseant action.

B. GHB

In other embodiments, the second moiety of the composition of the present invention is gamma-hydroxybutyric acid (GHB) or any analog, derivative, or variant of GHB. GHB is a naturally-occurring substance found in the central nervous system, wine, beef, small citrus fruits, and almost all animals in small amounts. GHB is naturally produced in the human body's cells and is structurally related to the ketone body beta-hydroxybutyrate. It is also a neuroprotective therapeutic nutrient that is categorized as an illegal drug in a number of countries. It is currently regulated in the US and used to treat cataplexy and excessive daytime sleepiness in patients with narcolepsy. As a supplement/drug, it is used most commonly in the form of a salt. GHB is also produced as a result of fermentation.

GHB has at least two distinct binding sites in the central nervous system. GHB is an agonist of GHB receptor, which is excitatory, (Wu Y, et. al., 2004, *Neuropharmacology* 47 (8): 1146-56.) and it is a weak agonist at the $GABA_B$ receptor, which is inhibitory. GHB is probably synthesized from GABA in GABAergic neurons, and released when the neurons fire.

If taken orally, GABA by itself crosses the blood-brain-barrier very poorly, nor do high concentrations very effectively reach the GABA receptors once inside the brain. Since GABA is naturally synthesized in the brain, a higher than normal concentration would be quickly metabolized. However, at pharmacological doses, GHB reaches much higher concentrations in the brain and activates $GABA_B$ receptors, which are primarily responsible for its sedative effects (Dimitrijevic N, et. al. 2005, *Eur. J. Pharmacol.* 519 (3): 246-52). GHB's sedative effects are blocked by $GABA_B$ antagonists.

Activation of both the GHB receptor and $GABA_B$ is responsible for the addictive profile of GHB. GHB's effect on dopamine release is biphasic, and low concentrations stimulate dopamine release via the GHB receptor. Higher concentrations inhibit dopamine release via $GABA_B$ receptors as do other $GABA_B$ agonists such as baclofen and phenibut (Maitre M, et. al. 1990, *J. Pharmacol. Exp. Ther.* 255 (2): 657-63; Smolders I, et. al., 1995 *Eur. J. Pharmacol.* 284 (1-2): 83-91). After the initial phase of inhibition, dopamine release is then increased via the GHB receptor. Both the inhibition and increase of dopamine release by GHB are inhibited by opioid antagonists such as naloxone and naltrexone.

Other prodrug ester forms of GHB include but are not limited to 1,4-diacetoxybutane, methyl-4-acetoxybutanoate and ethyl-4-acetoxybutanoate. These prodrugs of GHB presumably have delayed onset and longer duration of action. The intermediate compound 4-hydroxybutaldehyde is also a prodrug for GHB.

GHB can be made from ingredients such as GBL (gamma-butyrolactone), a solvent commonly used as a paint stripper, or butanediol (1,4-butanediol), a chemical used in the production of plastics and adhesives. Both GBL and butanediol are metabolized into GHB in the body.

It should be noted that the present invention encompasses GHB, any analog, derivative, prodrug form, or any other suitable variant of GHB.

III. Synthesis of GABA-Drug Conjugates

The GABA-Drug conjugates of the invention may be obtained via the synthetic methods illustrated in Schemes 1-8. Those of skill in the art will appreciate that a preferred synthetic route to the GABA-Drug conjugates of the invention consists of linking an analgesic drug selected from narcotics, NSAIDs, dual-acting opioid analgesics, antidepressant, γ-butyric acid and NMDA receptor antagonists to a GABA analog. Numerous methods have been described in the art for the synthesis of GABA analogs (Satzinger et al., U.S. Pat. No. 4,024,175; Silverman et al., U.S. Pat. No. 5,563,175; No. 6,028,214; No. 6,117,906; Silverman et al., International Publication WO 92/09560; No. WO 93/23383; Horwell et al., U.S. Pat. No. 6,020,370; No. 6,103,932; Horwell et al., International Publication No. WO 97/29101; WO 97/33858; WO 97/33859; Bryans et al., International Publication No. WO 98/17627; WO 99/21824; WO 99/31057; WO 99/31075; WO 99/61424; WO 00/15611; WO 00/31020; WO 00/50027; Guglietta et al., International Publication No. WO 99/08671; Belliotti et al., International Publication No. WO 99/31074). Other methods are known in the art for synthesizing GABA analogs, which are readily accessible to the skilled artisan. The analgesics described herein, are known in the art and may be prepared according to the known procedures. The art of linking an analgesic molecule containing various functional groups (e.g. carboxylic acid, hydroxyl, thiol, amine, sulfonamide) to a GABA analog is also well known by established procedures (See e.g., Green et al., "Protective Groups in Organic Chemistry", (Wiley, 2$^{nd}$ ed. 1991); Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995, Bodanzsky, "Principles of Peptide Synthesis," Springer Verlag, 1984; Bodanzsky, "Practice of Peptide Synthesis," Springer Verlag, 1984).

Accordingly, starting materials useful for preparing compounds of the invention and intermediates thereof are commercially available or can be prepared by well-known synthetic methods. Other methods for synthesis of the GABA-Drug conjugates described herein are either described in the art or will be readily apparent to the skilled artisan in view of the references provided hereinabove and may be used to synthesize the GABA-Drug conjugates of the invention. Accordingly, the methods presented in the Schemes described herein are illustrative rather than comprehensive.

In one aspect, the present invention provides a GABA-drug conjugate in which the first moiety of the conjugate e.g. a GABA analog is linked via an amino or N-terminus, or an acidic terminus other than a carboxylic acid group of the first moiety to the second moiety, e.g. a drug. In some embodiments, the first moiety is linked via the amino-terminus to the second moiety. In other embodiments, the first moiety is linked to the second moiety via an acidic group including but not limited to a phosphic acid group and a sulfinic acid group.

In some instances, GABA analogs undergo intra-molecular cyclization of the gamma amino group with the carboxyl functionality to form gamma-lactam, which is a cyclic amide, especially when carboxyl group is protected by esters. Formation of this side product, a lactam, may potentially generate toxicity in vivo. Therefore, in some embodiments, linking the two moieties through the amino group will potentially minimize side effects by reducing or preventing the formation of lactams in vivo as well as during the synthesis of the conjugate.

In any of the Schemes below, after the amino group of a GABA analog has been linked to a second moiety, which may be an analgesic drug or other protecting group, the carboxylic acid group may be converted to an ester or thioester by many synthetic methods, which are well-known to the skilled artisan. In one preferred embodiment, GABA analogs may be reacted with an alcohol or thiol in the presence of a coupling reagent (e.g., carbodiimide and dimethylaminopyridine) to provide the ester. In another preferred embodiment, GABA analogs may be reacted with an alkyl halide in the presence of base to yield the ester. Other methods for converting GABA analogs to esters or thioesters are well within the purview of the skilled artisan in view of the references provided herein.

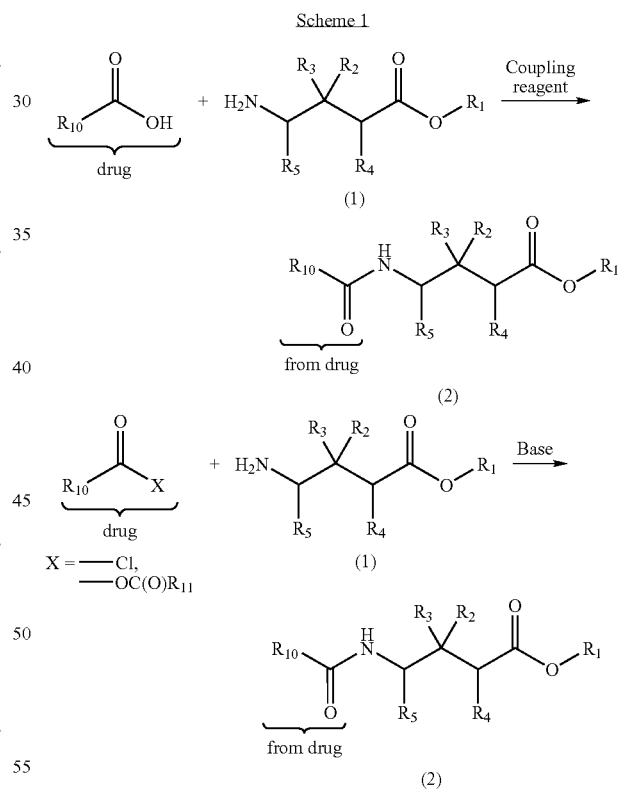

As illustrated above in Scheme 1, a drug containing carboxylic acids can be directly coupled to the terminal amino group of a GABA analog derivative (1) to provide adducts (2). Reagents for effecting this reaction are well known to the skilled artisan and include, but are not limited to, carbodiimides, aminium salts, phosphonium salts, and the like. Alternatively, reaction of carboxylic acid from drug can be activated by forming acyl chlorides, anhydrides followed with GABA analogs (1) in the presence of a base (e.g., hydroxide, tertiary amines, etc.) may be used to synthesize (2).

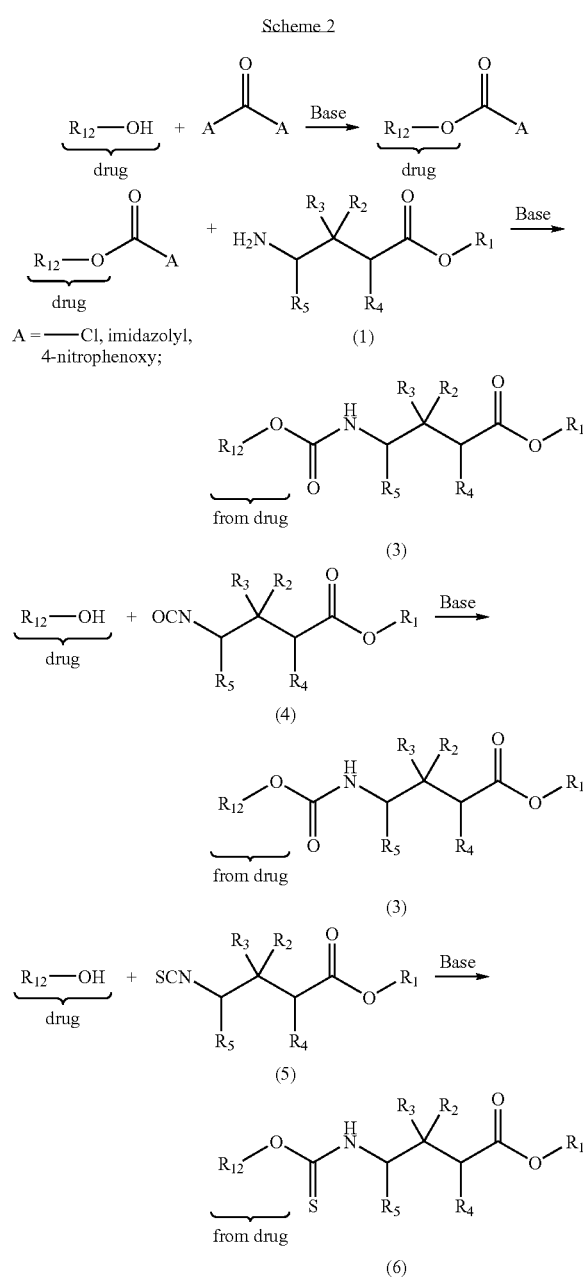

As illustrated in Scheme 2, GABA analog derivatives (1) and drug that contains hydroxyl moiety may be linked through carbamate or thiocarbamate linker by first reacting alcohol with phosgene, diimidazole carbamate or di-p-nitrophenyl carbonate in the presence of a base, followed by addition of GABA analogs under basic condition. Alternatively, the well-known addition of alcohols to isocyanates (4) or thioisocyanate (5) may also be used to synthesize (3) and (6).

One method for synthesis of GABA-Drug conjugate of Formula (8) is illustrated in Scheme 3. Choroformate is first treated with an aromatic leaving group such as p-nitrophenol in the presence of a base to provide p-nitrophenylcarbonate which the reacts with drugs containing carboxylic acid in the presence of sodium iodide and a base (tertiary amines, $Cs_2CO_3$, $Ag_2CO_3$) to afford compound (7). Treatment of the intermediate (7) with GABA analogs in the presence of a base leads to the formation of GABA-Drug conjugate of formula (8).

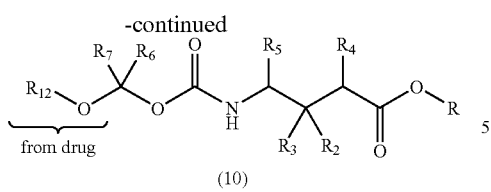

(10)

The synthesis of GABA-Drug conjugate of Formula (10) is illustrated in Scheme 4. Choroformate is first treated with a GABA analog in the presence of a base to provide intermediate (9), which then reacts with drugs containing hydroxyl group in the presence of sodium iodide and a base to afford the final GABA-Drug conjugate (10).

Scheme 5

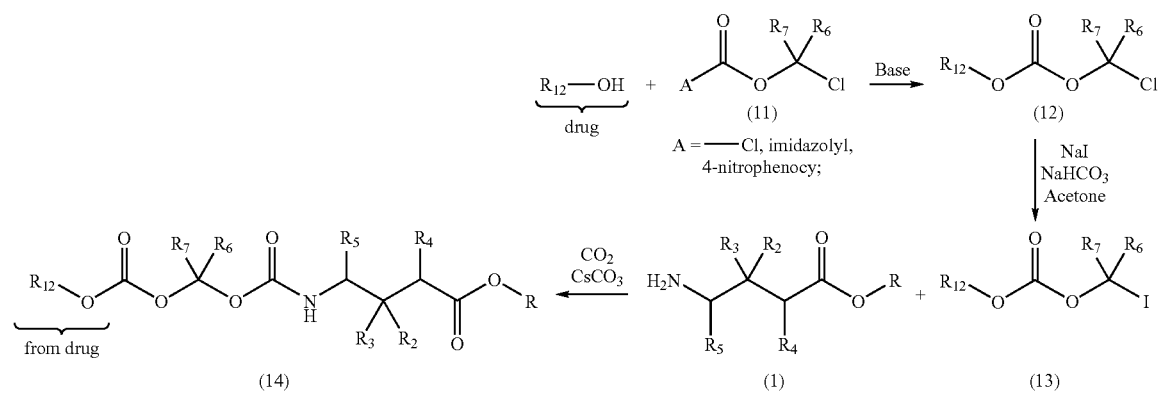

A method for synthesis of GABA-Drug conjugate with Formula (14) is illustrated in Scheme 5. A drug containing a hydroxyl function first reacts with choroformate (or other active carbamate or carbonate) in the presence of a base. Halide interchange provide intermediate (13), which reacts with GABA analogs under basic condition in the presence of carbon dioxide to afford the final GABA-Drug conjugate with formula (14).

Scheme 6

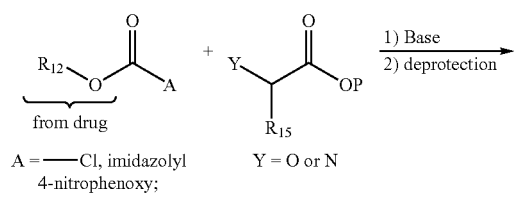

A = —Cl, imidazolyl
4-nitrophenoxy;

Y = O or N

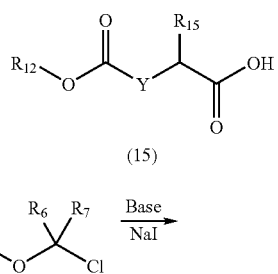

(15)

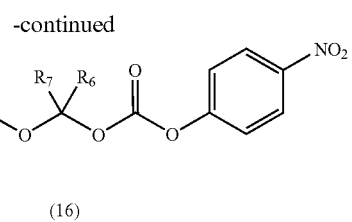

(16)

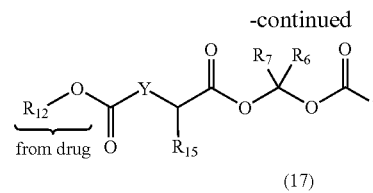

-continued

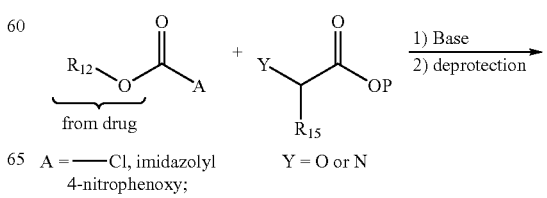

(17)

A method for synthesis of GABA-Drug conjugate with Formula (17) is illustrated in Scheme 6. An activated choroformate (or other active carbamate or carbonate) derived from a drug is reacted with α-hydroxy alkyl acetate in the presence of a base to provide carbonate. The ester is then removed to provide intermediate (15). The compound (15) reacts with halide substituted carbonate in the presence of a base and sodium iodide to form compound (16). The compound (16) is then coupled with a GABA analog under basic condition to afford the final compound with formula (17).

Scheme 7

A = —Cl, imidazolyl
4-nitrophenoxy;

Y = O or N

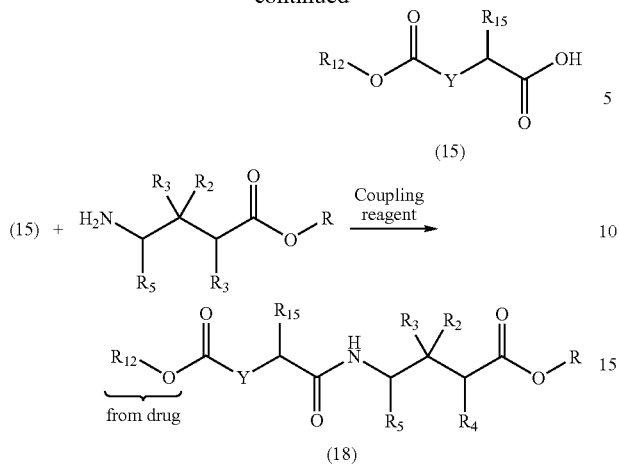

chloride in the presence of a base. After deprotection of ester (19), the free carboxylic acid (20) is then reacted with chloride under a basic condition to afford the final drug conjugate with the amino group protected to prevent lactam formation.

Linkers

In the present invention, the first moiety is covalently linked to the second moiety. In some embodiments, the two moieties are linked via a linker. Linkers that may be used in this invention include but are not limited to the following:

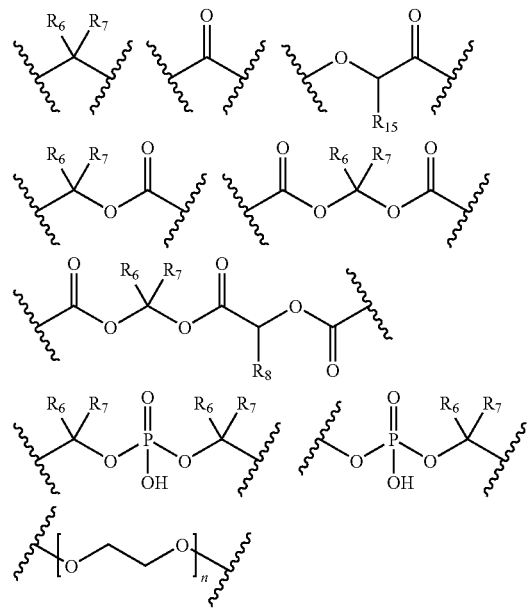

The synthesis of GABA-Drug conjugate with Formula (18) is illustrated in Scheme 7. An activated choroformate (or other active carbamate or carbonate) derived from a drug is reacted with α-hydroxy alkyl acetate under basic conditions, followed by removal of ester to provide compound (15). The ester in compound (15) is then coupled with a GABA analog to afford the final compound with formula (18).

In another aspect, the present invention provides a GABA-drug conjugate in which the first moiety of the conjugate e.g. a GABA analog is linked via the carboxyl, i.e. carboxlylic acid group, of the first moiety to the second moiety, e.g. a drug, and the amino i.e. N-terminus of the first moiety is linked to a protection group. Such structure of the conjugate prevents or reduces the formation of lactam, which may contribute to increased side effects and toxicity.

The protection group comprises an amino acid, an imine, a carbamate, an N-dithiasuccinimide, a mono- or di-alkyl phosphoramidate, or an acyloxycarbamate.

The physiologically labile linkage may be any suitable linkage that is labile under physiological conditions approxi-

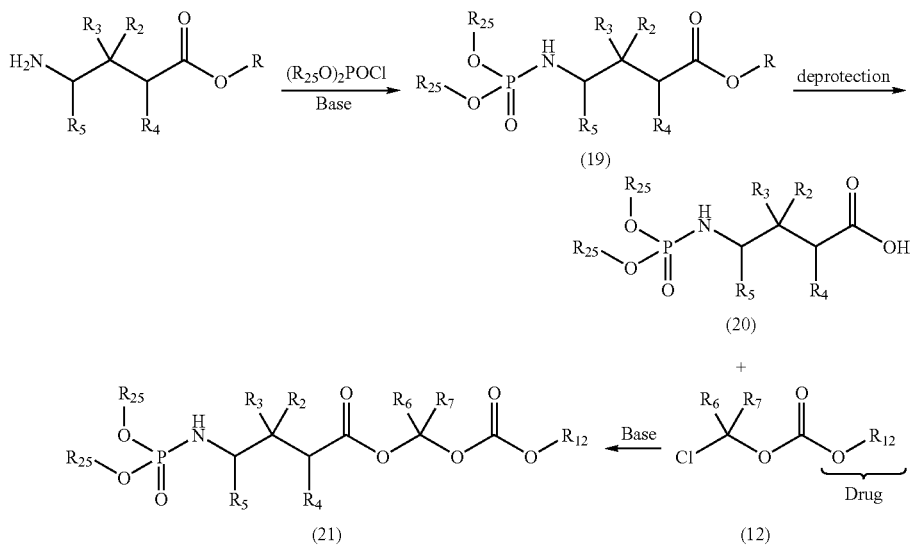

The synthesis of a GABA-Drug conjugate via the carboxyl group with Formula (21) is illustrated in Scheme 8. The starting GABA analog is first reacted with dialkyl phosphate mating those found in physiologic fluids, such as blood plasma. The linkage may be a direct bond (for instance, an amide, ester, carbonate, carbamate, acyloxycarbamate, sufonate, or a sulfamate linkage) or may be a linking group (for instance a $C_1$-$C_{12}$ dialcohol, a $C_1$-$C_{12}$ hydroxylalkanoic acid, a $C_1$-$C_{12}$ hydroxyalkylamine, a $C_1$-$C_{12}$ diacid, a $C_1$-$C_{12}$ aminoacid, or a $C_1$-$C_{12}$ diamine). Especially preferred linkages are direct amide, ester, carbonate, carbamate, and sulfamate linkages, and linkages via succinic acid, salicylic acid, diglycolic acid, oxa acids, oxamethylene, and halides thereof. The linkages are labile under physiologic conditions, which generally means pH of about 6 to about 8. The lability of the linkages depends upon the particular type of linkage, the precise pH and ionic strength of the physiologic fluid, and the presence or absence of enzymes that tend to catalyze hydrolysis reactions in vivo. In general, lability of the linkage in vivo is measured relative to the stability of the linkage when the compound has not been solubilized in a physiologic fluid. Thus, while some compounds according to the present invention may be relatively stable in some physiologic fluids, nonetheless, they are relatively vulnerable to hydrolysis in vivo (or in vitro, when dissolved in physiologic fluids, whether naturally occurring or simulated) as compared to when they are neat or dissolved in non-physiologic fluids (e.g. non-aqueous solvents such as acetone). Thus, the labile linkages are such that, when the drug is dissolved in an aqueous solution, especially a physiologic fluid such as blood plasma, the reaction is driven to the hydrolysis products.

While diacids, dialcohols, amino acids, and the like are described above as being suitable linkers, other linkers are encompassed within the present invention. For instance, while the hydrolysis product of a compound according to the present invention may comprise a diacid, the actual reagent used to make the linkage may be, for example, a diacylhalide, such as succinyl chloride, or an anhydride, such as succinic anhydride or diglycolic anhydride. A person having skill in the art will recognize that other possible acid, alcohol, amino, sulfato, and sulfamoyl derivatives may be used as reagents to make the corresponding linkage.

IV. Pharmaceutical Composition of the Invention

Yet another aspect of the present invention relates to formulations, routes of administration and effective doses for pharmaceutical compositions comprising a GABA-drug covalent conjugate or combination of the conjugates with other agents of the instant invention.

Compounds of the invention may be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including but not limited to those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation may contain at least one preservative. General methodology on pharmaceutical dosage forms is found in Ansel et al., Pharmaceutical Dosage Forms and Drug Delivery Systems (Lippencott Williams & Wilkins, Baltimore Md. (1999)). It will be recognized that, while any suitable carrier known to those of ordinary skill in the art may be employed to administer the compositions of this invention, the type of carrier will vary depending on the mode of administration.

Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug may be adjusted, the pH of the solution buffered and the isotonicity adjusted to be compatible with intravenous injection, as is well known in the art.

The compounds of the invention may be formulated as a sterile solution or suspension, in suitable vehicles, well known in the art. The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration. Suitable formulations and additional carriers are described in Remington "The Science and Practice of Pharmacy" ($20^{th}$ Ed., Lippincott Williams & Wilkins, Baltimore Md.), the teachings of which are incorporated by reference in their entirety herein.

The agents or their pharmaceutically acceptable salts may be provided alone or in combination with one or more other agents or with one or more other forms. For example a formulation may comprise one or more agents in particular proportions, depending on the relative potencies of each agent and the intended indication. For example, in compositions for targeting two different host targets, and where potencies are similar, about a 1:1 ratio of agents may be used. The two forms may be formulated together, in the same dosage unit e.g., in one cream, suppository, tablet, capsule, aerosol spray, or packet of powder to be dissolved in a beverage; or each form may be formulated in a separate unit, e.g., two creams, two suppositories, two tablets, two capsules, a tablet and a liquid for dissolving the tablet, two aerosol sprays, or a packet of powder and a liquid for dissolving the powder, etc.

Typical pharmaceutically acceptable salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it may be converted into a pharmaceutically acceptable addition salt with inorganic or organic bases. Examples of suitable bases include, but are not limited to, sodium hydroxide, potassium hydroxide, ammonia, cyclohexylamine, dicyclohexyl-amine, ethanolamine, diethanolamine, triethanolamine, and the like.

A pharmaceutically acceptable ester or amide includes, but is not limited to, ethyl, methyl, isobutyl, ethylene glycol, and the like. Typical amides include, but are not limited to, unsubstituted amides, alkyl amides, dialkyl amides, and the like.

If necessary or desirable, the conjugate and/or combinations of conjugates may be administered with other agents. The choice of agents that can be co-administered with the conjugate and/or combinations of conjugates of the instant invention can depend, at least in part, on the condition being treated. Agents of particular use in the formulations of the present invention include, but are not limited to, for example, any agent having a therapeutic effect for pain, including, but not limited to, e.g., drugs used to treat inflammatory conditions, depression, schizophrenia, insomnia, and anxiety.

The agent(s) (or pharmaceutically acceptable salts, esters or amides thereof) may be administered per se or in the form of a pharmaceutical composition wherein the active agent(s) is in an admixture or mixture with one or more pharmaceutically acceptable carriers. A pharmaceutical composition, as used herein, may be any composition prepared for administration to a subject. Pharmaceutical compositions for use in accordance with the present invention may be formulated in conventional manner using one or more physiologically acceptable carriers, comprising excipients, diluents, and/or auxiliaries, e.g., which facilitate processing of the active agents into preparations that can be administered. Proper formulation may depend at least in part upon the route of administration chosen. The agent(s) useful in the present invention, or pharmaceutically acceptable salts, esters, or amides thereof, can be delivered to a patient using a number of routes or modes of administration, including but not limited to oral, buccal, topical, rectal, transdermal, transmucosal, subcutaneous, intravenous, and intramuscular applications, as well as by inhalation.

Preferred compositions of the invention are formulated for oral delivery, particularly for oral sustained release administration. For oral administration, the GABA-drug conjugate can be formulated readily by combining the active GABA-drug conjugate with pharmaceutically acceptable carriers well known in the art. Such carriers enable the GABA-drug conjugate of the invention to be formulated as tablets, including but not limited to chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including but not limited to solid diluents or fillers, sterile aqueous media and various non-toxic organic solvents. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the agents of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage. Moreover, in a tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used.

Aqueous suspensions for oral use may contain conjugate(s) of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like. Suitable carriers, excipients or diluents include but are not limited to water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

In some embodiments, oils or non-aqueous solvents may be required to bring the agents into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands may also be attached to the liposomes to direct these compositions to particular sites of action. GABA-drug conjugates of this invention may also be integrated into foodstuffs, e.g., cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including but not limited to lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The GABA-drug conjugates may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active GABA-drug conjugates.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for administration.

Other forms suitable for oral administration include liquid form preparations including but not limited to emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Suitable fillers or carriers with which the compositions can be administered include but are not limited to agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

When formulating compounds of the invention for oral administration, it may be desirable to utilize gastroretentive formulations to enhance absorption from the gastrointestinal (GI) tract. A formulation which is retained in the stomach for several hours may release compounds of the invention slowly and provide a sustained release that may be preferred in some embodiments of the invention. Disclosure of such gastroretentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques may be utilized to maximize absorption of the compounds of the invention.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol.

For injectable formulations, the vehicle may be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation may also comprise polymer compositions which are biocompatible, biodegradable, such as poly(lactic-co-glycolic)acid. These materials may be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

When administration is by injection, the active compound may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the active compound may be in powder form for constitution with a suitable vehicle, e.g., sterile pyrogen-free water, before use. In some embodiments, the pharmaceutical composition does not comprise an adjuvant or any other substance added to enhance the immune response stimulated by the GABA-drug conjugate. In some embodiments, the pharmaceutical composition comprises a substance that inhibits an immune response to the GABA-drug conjugate. Methods of formulation are known in the art, for example, as disclosed in Remington's Pharmaceutical Sciences, latest edition, Mack Publishing Co., Easton P.

In addition to the formulations described previously, the agents may also be formulated as a depot preparation. Such long acting formulations may be administered by implantation or transcutaneous delivery (for example subcutaneously or intramuscularly), intramuscular injection or use of a transdermal patch. Thus, for example, the GABA-drug conjugates may be formulated with suitable polymeric or hydrophobic materials (for example as an emulsion in an acceptable oil) or ion exchange resins, or as sparingly soluble derivatives, for example, as a sparingly soluble salt.

In some embodiments, pharmaceutical compositions comprising one or more GABA-drug conjugates of the present invention exert local and regional effects when administered topically or injected at or near particular sites of pain. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, may be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations may also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In some embodiments, local/topical formulations comprising an enzyme inhibitor are used to treat epidermal or mucosal viral infections.

Pharmaceutical compositions of the present invention may contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents of the instant invention may be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

The compositions according to the present invention may be in any form suitable for topical application, including but not limited to aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions may also consist of solid preparations constituting soaps or cleansing bars.

Compositions of the present invention may also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants may be introduced into the fatty phase, into the aqueous phase and/or into the lipid vesicles.

In some embodiments, pain associated with eye can be effectively treated with ophthalmic solutions, suspensions, ointments or inserts comprising an agent or combination of agents of the present invention. Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include but are not limited to isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions may be enhanced by a surfactant or other appropriate co-solvent in the composition. Such cosolvents include but are not limited to polysorbate 20, 60, and 80, Pluronic F68, F-84 and P-103, cyclodextrin, or other agents known to those skilled in the art. Such co-solvents may be employed at a level of from about 0.01% to 2% by weight.

The compositions of the invention may be packaged in multidose form. Preservatives may be preferred to prevent microbial contamination during use. Suitable preservatives include, but are not limited to: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives may be employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% may be sufficient to preserve the compositions of the present invention from microbial attack.

In some embodiments, pain associated with the ear can be effectively treated with otic solutions, suspensions, ointments or inserts comprising a GABA-drug conjugate or combination of GABA-drug conjugates of the present invention.

In some embodiments, the GABA-drug conjugates of the present invention are delivered in soluble rather than suspension form, which allows for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

In some embodiments relating to topical/local application, the pharmaceutical compositions can include one or more penetration enhancers. For example, the formulations may comprise suitable solid or gel phase carriers or excipients that increase penetration or help delivery of GABA-drug conjugates or combinations of GABA-drug conjugates of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include but are not limited to humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In some embodiments, the pharmaceutical compositions will include one or more such penetration enhancers.

In some embodiments, the pharmaceutical compositions for local/topical application can include one or more antimicrobial preservatives such as quaternary ammonium compounds, organic mercurials, p-hydroxy benzoates, aromatic alcohols, chlorobutanol, and the like.

Gastrointestinal pain can be effectively treated with orally- or rectally delivered solutions, suspensions, ointments, enemas and/or suppositories comprising a GABA-drug conjugate or combination of GABA-drug conjugates of the present invention.

Pain associated with the respiratory system can be effectively treated with aerosol solutions, suspensions or dry powders comprising a GABA-drug conjugate or combination of GABA-drug conjugates of the present invention. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising an enzyme inhibitor can be dissolved, suspended or emulsified in a propellant or a mixture of solvent and propellant, e.g., for administration as a nasal spray or inhalant. Aerosol formulations may contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the agent or combination of agents of the present invention is carried into the respiratory tree of the subject when administered by the nasal or oral respiratory route Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S.

Pat. No. 5,776,434, issued Jul. 7, 1998. Hydrocarbon propellants useful in the invention include, but are not limited to, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of a GABA-drug conjugate of the invention such as an enzyme inhibitor in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation may comprise a suspension of an agent or combination of agents of the instant invention, e.g., an enzyme inhibitor, and a dispersing agent. Dispersing agents useful in the invention include, for example, sorbitan trioleate, oleyl alcohol, oleic acid, lecithin and corn oil. A suspension aerosol formulation can also include but are not limited to lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as an agent or combination of agents of the invention, e.g., an enzyme inhibitor. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

The compounds of the invention may be formulated for administration as suppositories. A low melting wax, such as a mixture of triglycerides, fatty acid glycerides, Witepsol S55 (trademark of Dynamite Nobel Chemical, Germany), or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

It is envisioned additionally, that the compounds of the invention may be attached releasably to biocompatible polymers for use in sustained release formulations on, in or attached to inserts for topical, intraocular, periocular, or systemic administration. The controlled release from a biocompatible polymer may be utilized with a water soluble polymer to form a instillable formulation, as well. The controlled release from a biocompatible polymer, such as for example, PLGA microspheres or nanospheres, may be utilized in a formulation suitable for intra ocular implantation or injection for sustained release administration as well. Any suitable biodegradable and biocompatible polymer may be used.

When a GABA-Drug conjugate of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Pharmaceutical compositions comprising a GABA-Drug conjugate of the invention may be manufactured by means of conventional mixing, dissolving, granulating, dragee-making, levigating, emulsifying, encapsuling, entrapping or lyophilizing process.

V. Method of Treatment

The current invention provides prophylactic and therapeutic treatment methods by administration to a subject in need thereof a therapeutically effective amount of a compound or a pharmaceutical composition of the invention. In some embodiments, the compound of the invention comprises a first moiety and a second moiety, the first moiety being covalently linked via an amino terminus to the second moiety, wherein the first moiety is γ-aminobytyric acid (GABA) or an analog or derivative of GABA. In other embodiments, the compound of the invention used for prophylactic and/or therapeutic treatment of a disorder comprises a first moiety and a second moiety, the first moiety being covalently linked via a carboxyl terminus to the second moiety, and an amino terminus of the first moiety is linked to a protection group, wherein the first moiety is γ-aminobytyric acid (GABA) or an analog or derivative of GABA.

A suitable subject can be, e.g., a human, a non-human primate (including but not limited to a gorilla, chimpanzee, orangutan, or a monkey), a rodent (including but not limited to a mouse, rat, guinea pig, or gerbil) a dog, a cat, horse, cow, pig, sheep, rabbit, or goat. The subject is preferably a mammal, and most preferably a human.

In some embodiments, a GABA-Drug conjugate and/or a pharmaceutical composition of the invention is administered to a mammal, preferably a human, to treat a neurological disorder, epilepsy, or pain including but not limited to centrally mediated pain, peripherally mediated pain, structural or soft tissue injury related pain, progressive disease related pain (i.e., oncology) and a neuropathic pain state, all of which includes acute (i.e., acute injury or trauma, pre and post-surgical, headache such as a migraine), chronic (i.e., neuropathic pain conditions such diabetic peripheral neuropathy and post-herpatic neuralgia) and inflammatory condition (i.e., osteo or rheumatoid arthritis, sequela to acute injury or trauma) pain states, depression, anxiety, psychosis, faintness attacks, hypokinesia, cranial disorders, neurodegenerative disorders, panic, insomnia, gastrointestinal disorders, addictive disorders (e.g. ethanol, cocaine), restless leg syndrome.

In other embodiments, the GABA-Drug conjugates and/or compositions of the invention are administered to an animal, preferably a human, as a preventative/prophylactic measure against various disorders including predisposition for a neurological disorder, epilepsy, pain including but not limited to centrally mediated pain, peripherally mediated pain, structural or soft tissue injury related pain, progressive disease related pain (i.e., oncology) and neuropathic pain states, all of which would include acute (i.e., acute injury or trauma, pre and post-surgical, headache such as a migraine), chronic (i.e., neuropathic pain conditions such diabetic peripheral neuropathy and post-herpatic neuralgia) and inflammatory condition (i.e., osteo or rheumatoid arthritis, sequela to acute injury or trauma) pain states, depression, anxiety, psychosis, faintness attacks, hypokinesia, cranial disorders, neurodegenerative disorders, panic, insomnia, gastrointestinal disorders, addictive disorders (e.g. ethanol, cocaine), and restless leg syndrome.

In further embodiments, the GABA-Drug conjugates and/or compositions of the invention are used for the prevention of one disorder and concurrently for the treatment of another disorder mentioned hereinabove, for example, a GABA-drug conjugate can be used for the prevention of psychosis or addiction and the treatment of pain.

The suitability of the GABA-Drug conjugates and/or compositions of the invention in treating and/or preventing a neurological disorder, epilepsy and pain includes, but is not limited to, centrally mediated pain, peripherally mediated pain, structural or soft tissue injury related pain, progressive disease related pain (i.e., oncology) and neuropathic pain states, all of which includes acute (i.e., acute injury or trauma, pre and post-surgical, headache such as a migraine), chronic (i.e., neuropathic pain conditions such diabetic peripheral neuropathy and post-herpatic neuralgia) and inflammatory (i.e., osteo or rheumatoid arthritis, sequela to acute injury or trauma) pain states. Therapeutic and prophylactic treatment regimens for the abovementioned diseases including but not limited to depression, anxiety, psychosis, faintness attacks, hypokinesia, cranial disorders, neurodegenerative disorders, panic, insomnia, gastrointestinal disorders, addictive disorders (e.g. ethanol, cocaine), and restless leg syndrome may be determined by methods described in the art (Satzinger et al., U.S. Pat. No. 4,04,175; Silverman et al., U.S. Pat. Nos. 5,563, 175; 6,028,214; 6,117,906; International Publication No. WO92/09560; 93/23383; Horwell et al., U.S. Pat. No. 6,020, 370; International Publication No. WO97/29101, 97/33858; 97/33859; Bryans et al., International Publication No. WO99/ 31057; 99/31075; 99/61424; 00/15511; 00/31020; 00/50027; 02/00209; Guglietta et al. International Publication No. WO 99/08671; Andrea et al., International Publication No. WO99/ 12537; Ashburn et al., International Publication No. 08/11016; Rosenburg et al., International Publication No. 08/09663; Buschmann et al., International Publication No. WO07/90661; Garcia et al. International Publication WO07/ 52999; Rao et al., International Publication No. WO07/ 38620; Wong et al., International Publication WO06/113568; Hizue et al., International Publication No. WO05/102390; Field et al., International Publication No. WO05/92318; Hurtt et al., International Publication No. WO00/53225).

Administration

The GABA-Drug conjugates and/or compositions of the present invention may be administered or applied singly, in combination with one or more pharmaceutically active agents, including but not limited to other compounds of the invention.

The present GABA-Drug conjugates and/or compositions of the invention, which comprise one or more compounds of the invention, are preferably administered via oral administration. The GABA-Drug conjugates and/or compositions of the invention may also be administered via any parenteral route, for example, by infusion or bolus injection, by absorption through epithelial or mucocutaneous linings (e.g. oral mucosa, rectal and intestinal mucosa, etc.). Administration can be systemic or local. Various delivery systems are known for use in administering a GABA-Drug conjugate and/or composition of the invention, for example, encapsulation in liposomes, microparticles, microcapsules, capsules, etc. Methods of administration include, but are not limited to, intradermal, intramuscular, intraperitoneal, intravenous, subcutaneous, intranasal, epidural, oral, sublingual, intracerbral, intravaginal, transdermal, rectally, inhalation, topically, particularly to the ears, nose, eyes, or skin, as described in Section IV hereinabove. The GABA-Drug conjugates and/or compositions of the present invention may be administered or applied singly, or in combination with one or more pharmaceutically active agents, including but not limited to other compounds of the invention.

In some preferred embodiments, the GABA-Drug conjugates and/or compositions of the invention can be delivered via a sustained release system, preferably an oral sustained release system. In one embodiment, a pump may be used (see Langer, supra; Sefton, 1987, *CRC Crit Ref Biomed Eng.* 14, 201; Saudek et al., 1989, N. Engl. *J. Med.* 321, 574). In another embodiment, polymeric materials can be used (see "Medical Applications of Controlled Release," Langer and Wise (eds.), *CRC Pres.*, Boca Raton, Fla. (1974); "Controlled Drug Bioavailability," Drug Product Design and Performance, Smolin and Ball (eds.), Wiley, N.Y. (1984); Ranger and Peppas, 1983, *J. Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In a preferred embodiment, polymeric materials are used for an oral sustained release delivery. Preferred polymers include but are not limited to sodium carboxymethylcellulose, hydroxypropylcellulose, hydroxypropylmethylcellulose and hydroxyethylcellulose, most preferably, hydroxypropylmethylcellulose. Other preferred cellulose ethers have also been described (Alderman, Int. *J. Pharm. Tech. & Prod. Mfr.,* 1984, 5(3) 1-9). Factors affecting drug release are well known to a skilled artisan and have been described in the art (Bamba et al., *Int. J. Pharm.,* 1979, 2, 307).

In other embodiments, enteric-coated preparation can be used for oral sustained release administration. Preferred coating materials include but are not limited to polymers with a pH-dependent solubility (i.e., pH-controlled release), polymers with a slow or pH-dependent rate of swelling, dissolution or erosion (i.e. time-controlled release), polymers that form firm layers that are destroyed by an increase in pressure (i.e. pressure-controlled release).

In still other embodiments, osmotic delivery systems are used for oral sustained release administration (Verma et al., *Drug Dev. Ind, Pharm.,* 2000, 26:695-708). In a preferred embodiment, OROS™ osmotic devices are used for oral sustained release delivery devices (Theeuwes et al., U.S. Pat. No. 3,845,770; No. 3,916,899).

In yet another embodiment, a controlled-released system can be placed in proximity of the target of the GABA-Drug conjugates and/or composition of the invention, thus requiring only a fraction of the systemic dose (e.g., Goodson, in "*Medical Applications of Controlled Release*," supra, vol. 2, pp. 115-138 (1984)). Other controlled-released systems discussed in Langer, 1990, *Science* 249: 1527-1533 may also be used.

The GABA-Drug conjugates and/or compositions of the invention may be cleaved either chemically and/or enzymatically. One or more enzymes present in the stomach, intestinal lumen, intestinal tissue, blood, liver, brain or any other suitable tissue of a mammal may enzymatically cleave the linker of the GABA-Drug conjugates and/or compositions of the invention. The mechanism of cleavage of GABA-Drug may be one that is known in the art or one that is unknown or novel to the relevant field. The liners of GABA-Drug conjugates and/or compositions of the invention may be cleaved prior to absorption by the gastrointestinal tract and/or after absorption by the gastrointestinal tract (e.g. in intestinal tissue, blood, liver or other suitable tissue of a mammal). If the linkers of GABA-Drug conjugates in invention are cleaved prior to absorption by the gastrointestinal tract, the drugs and GABA analogs may be absorbed into the systemic circulation conventionally by active transport and/or passive diffusion.

Dosage

Pharmaceutical compositions suitable for use in the present invention include compositions wherein the active ingredients are present in an effective amount, i.e., in an amount effective to achieve therapeutic and/or prophylactic benefit in a host with at least one type of pain or a neurological disorder. An effective amount of GABA-Drug conjugate of the invention is intended for use to treat or prevent a disorder including but not limited to pain (i.e., oncology), a neuropathic pain state encompassing acute (i.e., acute injury or trauma, pre and post-surgical, headache such as a migraine), chronic (i.e., neuropathic pain conditions such diabetic peripheral neuropathy and post-herpatic neuralgia) and inflammatory (i.e., osteo or rheumatoid arthritis, sequela to acute injury or trauma) pain state, depression, anxiety, psychosis, faintness attacks, hypokinesia, cranial disorders, neurodegenerative disorders, panic, insomnia, gastrointestinal disorders, addictive disorders (e.g. ethanol, cocaine), and restless leg syndrome.

The actual amount effective for a particular application will depend on the condition or conditions being treated, the condition of the subject, the severity of the affliction, the formulation, and the route of administration, as well as other factors known to those of skill in the art. In vitro or in vivo assays may optionally be employed to help identify the optimal dosage ranges. Determination of an effective amount of a GABA-drug conjugate is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. The GABA-Drug conjugates of the invention are preferably tested in at least one animal model to demonstrate safety and efficacy. In some embodiments, a therapeutically effective dose of GABA-Drug conjugate of the invention described herein provides therapeutic benefit without causing substantial toxicity while providing synergistic effect as compared to each individual compound dosed or two parent compounds co-formulated. Toxicity of GABA-Drug conjugates of the invention may be determined using standard pharmaceutical procedures and may be readily ascertained by the skilled artisan. The dose ratio between toxic and therapeutic effect is the therapeutic index. In some embodiments, a GABA-Drug conjugate of the invention exhibits higher therapeutic indices in treating a disease or a disorder mentioned herein as compared to their parent compounds. The dosage of a GABA-Drug conjugate is within a range of circulating concentrations that result in little or no toxicity. One skilled in the art can determine the effective amount for human use, especially in light of the animal model experiments described herein. Based on animal data, and other types of similar data, those skilled in the art can determine the effective amounts of compositions of the present invention appropriate for humans.

The effective amount when referring to a GABA-drug conjugate or combination of GABA-drug conjugates of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

In some embodiments, administration of GABA-drug conjugates of the present invention may be intermittent, for example administration once every two days, every three days, every five days, once a week, once or twice a month, and the like. In some embodiments, the amount, forms, and/or amounts of the different forms may be varied at different times of administration. For example, the dosage of a pharmaceutical composition of the present invention may be delivered by a single administration, multiple applications or a controlled release. In a preferred embodiment, the GABA-Drug conjugates of the invention are delivered by oral sustained release administration. Preferably, the GABA-Drug conjugate is administered once or twice per day. Suitable dosage range for oral administration is dependent on the potency of the parent GABA-Drug conjugate, but is generally about 0.001 mg to about 200 mg of a compound of the invention per kilogram body weight. Preferably, the dosage ranges from about 0.01 to about 50 mg/kg body, more preferably from about 0.05 to about 25 mg/kg body, more preferably from about 0.1 to about 10 mg/kg body, and more preferably from about 0.2 to about 5 mg/kg body. Dosing may be repeated intermittently, provided alone or in combination with other drugs. The schedule may continue for as long as an effective treatment of the disorder demands.

In one embodiment, the invention also provides a composition comprising a GABA analog-NSAID conjugate. The active NSAID upon release from the conjugate is present in an anti-inflammatory amount, preferably less than the amount normally used when administered alone, and the active GABA analog upon release from the conjugate is present in a cytoprotective amount, namely an amount which is effective in preventing or reducing the gastrointestinal damage otherwise caused by the NSAID. Yet both the GABA analog and the NSAID, in their active forms upon in vivo release from the conjugate, are present at a therapeutically effective dose that results in a superior therapeutic efficacy as compared to when the GABA analog and the NSAID are administered alone or co-formulated. In general, the GABA analog-NSAID is present at doses between 0.001 mg to about 200 mg. Any NSAID can be combined with any GABA analog according to this invention. Preferred GABA analogs to be employed are the compounds of Formulas (3) and (4), i.e. gabapentin and pregabalin. Preferred NSAIDs to be employed in the compositions include but are not limited to sulindac, naproxen, indomethacin, mefenamic acid, diclofenac, fenoprofen, diflunisal, etodolac, ibuprofen, piroxicam, acetylsalicylic acid, oxaprozin, and bromfenac. Most of the NSAIDs to be used are commercially available, generally as salts such as calcium, sodium, or potassium, for example, fensprofen calcium and bromfenac sodium. More preferred combinations include but are not limited to pregabalin or gabapentin conjugated with naproxen sodium or ibuprofen. The compositions may contain common pharmaceutical excipients such as those described above.

A person skilled in the art would be able to monitor in a patient the effect of administration of a particular agent. For example, pain scale can be determined by techniques standard in the art.

VII. Method of Use

A. Combination Therapy

In certain embodiments of the present invention, the GABA-Drug conjugates of the invention can be used in a combination therapy with at least one other therapeutic agent. The GABA-Drug conjugates of the invention and the therapeutic agent can act additively or, more preferably, synergistically.

Combination therapy includes the administration of a conjugate of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). Combination therapy may be carried out either sequentially or substantially simultaneously. In the case of sequential administration of more than one therapeutic agent, each therapeutic agent is administered at a different time. In the case of simultaneous administration, at least two of the therapeutic agents are administered in a substantially simultaneous manner, either in the same pharmaceutical composition or in different pharmaceutical compositions. Substantially simultaneous administration can be accomplished, for example, by administering to the subject a single capsule having a fixed ratio of each therapeutic agent or in multiple, single capsules for each of the therapeutic agents. In a preferred embodiment, a composition comprising a GABA-Drug conjugate of the invention is administered concurrently with the administration of another therapeutic agent, which can be part of the same composition as the GABA-Drug conjugates of the invention or a different composition. In another embodiment, a composition comprising a GABA-Drug conjugate of the invention is administered prior to, or subsequent to, administration of another therapeutic agent.

Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. Combination therapy also encompasses the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, by a significant period of time. The conjugate and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

B. Reduction of Adverse Effects and Enhancement of Therapeutic Efficacy

The present invention also embodies a method for reducing an adverse effect and/or increasing therapeutic efficacy associated with a treatment of a disorder by administering to a subject in need a therapeutically effective amount of a conjugate or pharmaceutical composition of the invention.

Toxicity and therapeutic efficacy of the conjugates described herein can be determined by standard pharmaceutical procedures in experimental animals, e.g., by determining the $IC_{50}$ and the $LD_{50}$ (lethal dose causing death in 50% of the tested animals) for a subject compound.

In one embodiment, the composition of the invention reduces the incidence of unwanted side effects caused by many of the pain treatment regimens including but not limited to gastrointestinal side effects, cognitive impairment, nausea, and constipation. In another embodiment, the composition of the present invention achieves adequate pain alleviation at a lower dose than that required for each individual unconjugated drug. In another embodiment, the composition of the present invention has improved pharmacokinetic and physiological properties including but not limited to slower systemic clearance and improved absorption of the GABA analogs, allowing these drugs to reach their full potential in treatment of pain and other CNS disorders. In yet another embodiment, the use of a sustained release formulation for delivery of the composition of the present invention further reduces the rapid systemic clearance of the active drugs, i.e. GABA analogs. Since GABA analogs, such as baclofen, gabapentin and pregabalin are absorbed in the small intestine by the neutral amino transporter systems rather than being absorbed in the large intestine, the composition of the present invention enables successful application of a sustained release approach to these GABA analogs.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Examples 1

Synthesis of Pregabalin-Naproxen Conjugates

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations stand for the following terms. An abbreviation that is not defined herein has its generally accepted meaning.

AIBN=2,2'-azobis(isobutyronitrile)
Atm=atmosphere
Boc=tert-butyloxycarbonyl
Cbz=carbobenzyloxy
CPM=counts per minute
DCC=dicyclohexylcarbodiimide
DMAP=4-N,N-dimethylaminopyridine
DMEM=Dulbecco's minimun eagle medium
DMF=N,N-dimethylformamide
DMSO=dimethylsulfoxide
Fmoc=9-fluorenylmethyloxycarbonyl
g=gram
h=hour
HBSS=Hank's buffered saline solution
L=liter
LC/MS=liquid chromatography/mass spectroscopy
M=molar
min=minute
mL=milliliter
mmol=millimoles
NBS=N-bromosuccinimide
NHS=N-hydroxysuccinimide
PBS=phosphate buffered saline
THF=tetrahydrofuran
TFA=trifluoroacetic acid
TMS=trimethylsilyl
μL=microliter
μM=micromolar
v/v=volume to volume Acyloxyalkylmethanethiocarbonates (3)

Step 1:

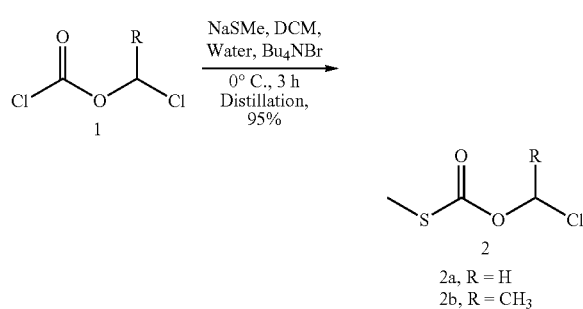

General Procedure:

A 21% (w/w) aqueous solution of sodium methylthiolate (58 g, 0.17 mol) was added to a solution of 1-chloroethyl chloroformate (25 g, 0.17 mol) and tetrabutylammonium bromide (1.7 mmol) in $CH_2Cl_2$ (45 mL) over 2 h. The reaction mixture was stirred for an additional hour, then worked-up by separating the aqueous phase and extracting the organic phase with brine (2×50 mL). The organic phase was dried over anhydrous sodium sulfate and concentrated in vacuo. The residue was purified by vacuum distillation to afford the product as a colorless liquid (yield, 95%). Compound 2a: $^1$H NMR (400 MHz, $CDCl_3$) δ 5.75 (s, 1H), 2.38 (s, 2H). Compound 2b: $^1$H NMR (400 MHz, $CDCl_3$) δ 6.59 (q, J=5.7 Hz, 1H), 2.37 (s, 3H), 1.80 (d, J=5.8 Hz, 3H).

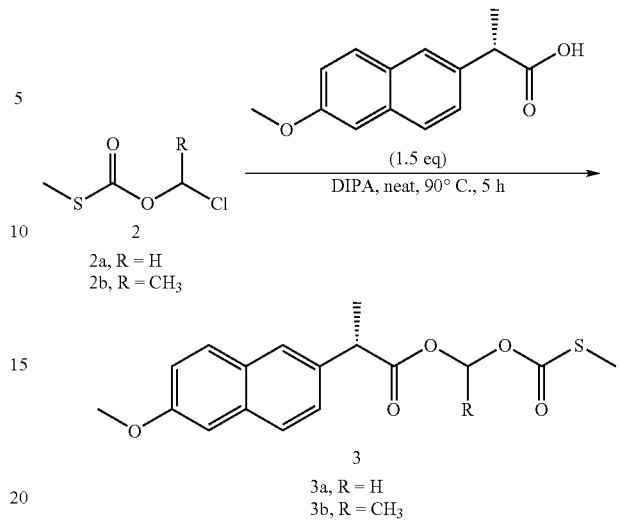

General Procedure:

Diisopropylamine (16 g, 150 mmol) was added dropwise to a mixture of (S)-6-Methoxy-alpha-methyl-2-naphthaleneacetic acid (naproxan, 34 g, 150 mmol) and chloroalkylmethanethiocarbonates (2, 100 mmol). The mixture was stirred at 80~90° C. for 3 hrs. Then 30 mL dichloromethane was added to the reaction mixture. The mixture was stirred for 2 hrs. The reaction mixture was then partitioned between 50 mL water and 100 mL ethyl ether. The organic phase was washed with water, saturated potassium carbonate solution ($K_2CO_3$) and brine, and then dried over anhydrous sodium sulfate ($Na_2SO_4$). After the solvent was removed by rotary evaporation and recrystallized in the mixture of methyl-tert-butyl ether (MTBE) and n-hexane, white solid product was obtained.

Compound (3a): white crystal, yield, 90%; mp: 73~74° C. $[α]^{25}_D$=+44.59°(c=1.0, $CH_2Cl_2$). IR (KBr) $ν_{max}$: 2981, 2936, 1757, 1723, 1633, 1606, 1506, 1485, 1454, 1393, 1266, 1176, 1157, 1065, 1030, 981, 854, 811, 673 $cm^{-1}$. $^1$H NMR (400 MHz, $CDCl_3$) δ 7.72 (s, 1H), 7.70 (s, 1H), 7.66 (d, J=1.3 Hz, 1H), 7.39 (dd, J=8.4, 1.7 Hz, 1H), 7.16 (dd, J=8.9, 2.5 Hz, 1H), 7.12 (d, J=2.4 Hz, 1H), 5.82 (d, J=5.6 Hz, 1H), 5.78 (d, J=5.6 Hz, 1H), 3.91 (q, J=7.1 Hz, 1H), 3.90 (s, 3H), 2.26 (s, 3H), 1.61 (d, J=7.2 Hz, 3H). $^{13}$C NMR (101 MHz, $CDCl_3$) δ 173.10, 171.05, 157.77, 134.68, 133.84, 129.35, 128.95, 127.34, 126.13 (2), 119.09, 105.59, 80.65, 55.30, 45.16, 18.29, 13.31.

Compound (3b, diastereoisomers): white crystal, yield: 87%; mp: 65~66° C. IR (KBr) $ν_{max}$: 3055, 2986, 2937, 2916, 2848, 1750, 1719, 1606, 1451, 1392, 1264, 1177, 1134, 1050, 910, 854, 747 $cm^{-1}$. $^1$H NMR (400 MHz, $CDCl_3$) δ 7.56 (d, J=2.8 Hz, 1H), 7.54 (t, J=2.1 Hz, 1H), 7.51 (s, 0.5H), 7.50 (s, 0.5H), 7.26-7.24 (m, 0.5H), 7.24-7.21 (m, 0.5H), 7.01 (t, J=2.2 Hz, 0.5H), 6.99 (t, J=2.2 Hz, 0.5H), 6.96 (s, 1H), 6.85 (dq, J=10.9, 5.4 Hz, 1H), 3.75-3.67 (m, 4H), 2.14 (s, 1.5H), 1.98 (s, 1.5H), 1.44 (d, J=1.6 Hz, 1.5H), 1.43 (d, J=1.6 Hz, 1.5H), 1.33 (d, J=5.5 Hz, 1.5H), 1.24 (d, J=5.5 Hz, 1.5H). $^{13}$C NMR (101 MHz, $CDCl_3$) δ 171.43, 171.32, 169.00, 168.80, 156.64, 156.60, 133.92, 133.79, 132.70, 132.66, 128.26, 128.21, 127.85 (2), 126.16, 126.08, 125.14, 125.02, 124.97 (2), 117.97, 117.85, 104.49, 104.46, 89.31, 89.05, 54.12 (2), 44.15, 44.11, 18.34, 18.24, 17.38, 17.18, 12.15, 11.97.

Step 2:

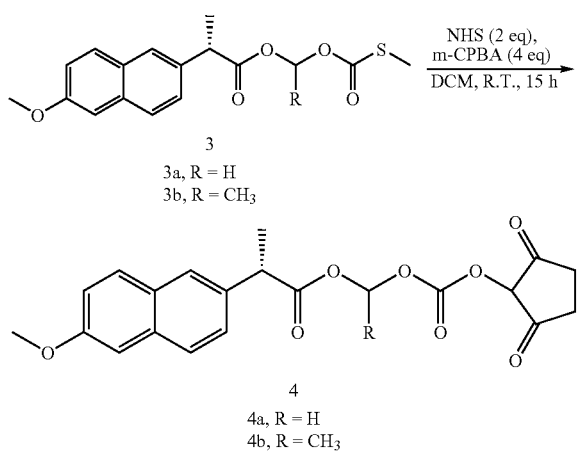

3
3a, R = H
3b, R = CH₃

4
4a, R = H
4b, R = CH₃

General Procedure:

N-hydroxysuccinimide (NHS, 2.30 g, 20 mmol) was added to compound (3) (10 mmol) dissolved in 15 mL dichloromethane and 2.1 g water. The resulting suspension was cooled to 0° C., 3-chloroperoxybenzoic acid (m-CPBA, 6.90 g, 40 mmol) dissolved in 25 mL dichloromethane was slowly added. The reaction mixture was then stirred at 0° C. for 1 hr and at room temperature for 15 hrs.

The reaction mixture was then filtered and diluted with 40 mL ethyl ether and 30 mL saturated potassium bicarbonate solution. The organic phase was separated and washed with saturated potassium carbonate solution (30 mL), water (40 mL) and brine (2×30 mL) and then dried over anhydrous sodium sulfate ($Na_2SO_4$). After the solvent was removed by rotary evaporation, the crude compound (4) was purified by silica gel column chromatography with 4:1 petrol ether (60-90° C.): ethyl acetate and recrystallized in ethyl acetate and n-hexane.

Compound (4a): yield: 32%, mp: 115–116° C.; $[a]^{25}_D$=+ 45.06° (c=1.0, $CH_2Cl_2$). IR (KBr) $v_{max}$: 2984, 2942, 1822, 1793, 1607, 1486, 1457, 1258, 1230, 1201, 1162, 1131, 1091, 986, 924, 813, 736, 645 $cm^{-1}$. $^1$H NMR (400 MHz, $CDCl_3$) δ 7.73 (d, J=4.1 Hz, 1H), 7.71 (d, J=4.4 Hz, 1H), 7.67 (s, 1H), 7.38 (dd, J=8.5, 1.7 Hz, 1H), 7.14 (dd, J=8.8, 2.5 Hz, 1H), 7.12 (d, J=2.2 Hz, 1H), 5.91 (d, J=5.5 Hz, 1H), 5.77 (d, J=5.5 Hz, 1H), 3.94 (q, J=7.1 Hz, 1H), 3.91 (s, 3H), 2.81 (s, 4H), 1.62 (d, J=7.2 Hz, 3H). $^{13}$C NMR (101 MHz, $CDCl_3$) δ 172.71, 168.47(2), 157.77, 150.73, 134.31, 133.82, 129.31, 128.83, 127.42, 126.18, 126.04, 119.11, 105.58, 83.74, 55.27, 44.97, 25.33(2), 18.21. HRMS (ESI) found 424.1002, ($[M+Na]^+$, calcd for $C_{20}H_{19}NO_8$ 424.1003).

Compound (4b, diastereoisomers): white crystal, yield, 40%; mp: 145–146 ° C. IR (KBr) $v_{max}$: 2992, 2942, 1819, 1792, 1744, 1632, 1606, 1506, 1486, 1454, 1393, 1373, 1260, 1234, 1202, 1048, 910, 879, 812, 735, 644 $cm^{-1}$. $^1$H NMR (400 MHz, $CDCl_3$) δ 7.71 (dd, J=8.5, 4.5 Hz, 2H), 7.65 (s, 1H), 7.38 (s, 0.5H), 7.36 (s, 0.5H), 7.17-7.08 (m, 2H), 6.88-6.79 (m, 1H), 3.98-3.83 (m, 4H), 2.82 (s, 2H), 2.73 (s, 2H), 1.58 (m, 4.5H), 1.48 (d, J=5.4 Hz, 1.5H). $^{13}$C NMR (101 MHz, $CDCl_3$) δ 172.31, 172.18, 168.39 (2), 168.24 (2), 157.75, 157.68, 149.87, 149.73, 134.66, 134.40, 133.80, 133.74, 129.45, 129.33, 128.93, 128.90, 127.36, 127.32, 126.18, 126.15 (2), 126.09, 119.09, 118.85, 105.58 (2), 93.89, 93.79, 55.33 (2), 45.27, 45.04, 25.44 (2), 25.29 (2), 19.27, 19.19, 18.41, 18.34. HRMS (ESI) found 438.1157, ($[M+Na]^+$, calcd for $C_{21}H_{21}NO_8$ 438.1159).

Step 3:

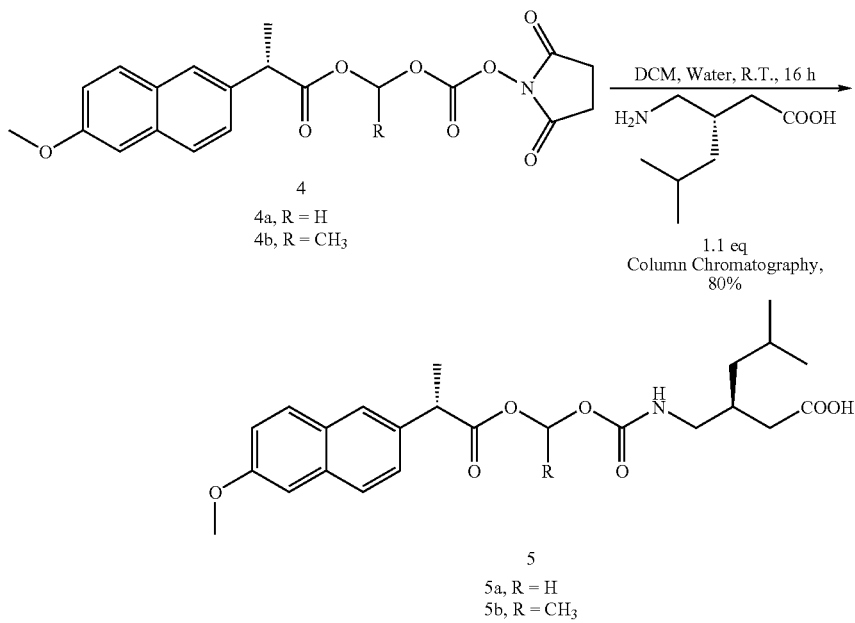

4
4a, R = H
4b, R = CH₃

5
5a, R = H
5b, R = CH₃

General Procedure:

(3S)-3-(Aminomethyl)-5-methylhexanoic acid (Pregabalin, 504 mg, 3.3 mmol) and 2 mL water was added to compound (4) (1.2 g, 3 mmol) dissolved in 5 mL dichloromethane. The mixture was stirred for 16 hrs at room temperature. The reaction mixture was diluted with 15 mL ethyl ether and 10 mL water. The organic phase was separated and washed with water (10 mL) and brine (2×10 mL) and then dried over anhydrous sodium sulfate ($Na_2SO_4$). After the solvent was removed by rotary evaporation, the crude product was purified by silica gel column chromatography with 4:1 petrol ether (60-90° C.): ethyl acetate to obtain viscose liquid compound.

Compound (5a): viscose liquid, yield, 80%. $[a]^{25}_D$=+17.79° (c=1.0, $CH_2Cl_2$). IR (KBr) $v_{max}$: 3351, 2960, 1746, 1634, 1607, 1535, 1464, 1392, 1265, 1218, 1175, 1159, 1123, 1032, 1000, 854, 738 $cm^{-1}$. $^1$H NMR (400 MHz, $CDCl_3$) δ 7.80-7.62 (m, 3H), 7.39 (dd, J=8.5, 1.5 Hz, 1H), 7.13 (dd, J=8.9, 2.4 Hz, 1H), 7.10 (d, J=1.9 Hz, 1H), 5.71 (d, J=5.8 Hz, 1H), 5.69 (d, J=5.9 Hz, 1H), 5.09 (t, J=6.3 Hz, 1H), 3.91 (s, 3H), 3.89 (q, J=7.2 Hz, 1H), 3.26-3.17 (m, 1H), 3.02 (dt, J=13.9, 7.0 Hz, 1H), 2.26 (dd, J=15.1, 5.0 Hz, 1H), 2.16 (dd, J=15.1, 7.6 Hz, 1H), 2.12-2.06 (m, 1H), 1.65-1.60 (m, 1H), 1.58 (d, J=7.1 Hz, 3H), 1.09 (t, J=7.6 Hz, 2H), 0.88 (d, J=6.6 Hz, 3H), 0.86 (d, J=6.6 Hz, 3H). $^{13}$C NMR (101 MHz, $CDCl_3$) δ 177.57, 173.97, 157.70, 154.90, 134.82, 133.77, 129.31, 128.90, 127.22, 126.19, 126.14, 119.05, 105.57, 80.09, 55.31, 45.22, 44.42, 41.26, 36.82, 33.41, 25.10, 22.61, 22.57, 18.24. HRMS (ESI) found 468.1995 ($[M+Na]^+$, calcd for $C_{24}H_{31}NO_7$ 468.1993).

Compound (5b): yield, 98%. HRMS (ESI) found 482.2145 ($[M+Na]^+$, calculated for $C_{25}H_{33}NO_7$ 482.2149). IR (KBr) $v_{max}$: 3340, 2956, 1741, 1633, 1606, 1529, 1507, 1454, 1391, 1264, 1231, 1175, 1160, 1066, 925, 854, 811, 747, 670 $cm^{-1}$.

Conditions for Chiral Purification:

The chiral purification was achieved using the conditions listed below. The fractions were collected and solvent was removed in vacuo to afford both diastoromers as white solid.

TABLE 1

| Column | CHIRALPAK AD-H |
|---|---|
| Column size | 0.46 cm I.D. × 15 cm L |
| Injection | 1 ul |
| Mobile phase | Hexane/EtOH = 60/40 (v/v) |
| Flow rate | 0.5 ml/min |
| Wave length | UV 220 nm |
| Temperature | 35° C. |
| Sample | X mg/ml in mobile phase |

TABLE 1-continued

| Brand of Sample | Hexane, EtOH:HPLC grade Racemate |
|---|---|

Compound (5b-1) (optical pure) as white crystal, mp: 100~101° C. $[a]^{25}_D$=+7.9°(c=1.0, $CHCl_3$). IR (KBr) $v_{max}$: 3368, 2956, 2937, 1741, 1633, 1607, 1531, 1508, 1464, 1392, 1264, 1232, 1175, 1155, 1069, 913, 734 $cm^{-1}$. $^1$H NMR (400 MHz, $CDCl_3$) δ 7.69 (d, J=8.6 Hz, 1H), 7.68 (s, 1H), 7.64 (s, 1H), 7.37 (d, J=8.4 Hz, 1H), 7.13 (d, J=9.1 Hz, 1H), 7.10 (s, 1H), 6.81 (q, J=5.2 Hz, 1H), 5.09 (s, 1H), 3.90 (s, 3H), 3.82 (q, J=6.9 Hz, 1H), 3.34-3.22 (m, 1H), 3.15-3.03 (m, 1H), 2.29 (m, 2H), 2.13 (m, 1H), 1.73-1.59 (m, 1H), 1.55 (d, J=7.0 Hz, 3H), 1.33 (d, J=5.0 Hz, 3H), 1.16 (t, J=6.5 Hz, 2H), 0.90 (d, J=6.9 Hz, 3H), 0.88 (d, J=6.6 Hz, 3H). $^{13}$C NMR (101 MHz, $CDCl_3$) δ 172.85, 157.65, 154.48, 135.35, 133.69, 129.29, 128.93, 127.17, 126.18, 126.03, 118.98, 105.59, 89.88, 55.31, 45.29, 44.35, 41.32, 37.09, 33.46, 29.71, 25.13, 22.67, 22.60, 19.51, 18.56.

Compound (5b-2) (optical pure) as white crystal, mp: 120~120° C. $[α]^{25}_D$=+23.62° (c=1.0, $CHCl_3$). IR (KBr) $v_{max}$: 3368, 2956, 2928, 1743, 1633, 1607, 1527, 1508, 1465, 1391, 1264, 1231, 1177, 1159, 1067, 913, 743 $cm^{-1}$. $^1$H NMR (400 MHz, $CDCl_3$) δ 7.71-7.68 (m, 2H), 7.65 (s, 1H), 7.38 (d, J=8.4 Hz, 1H), 7.13 (d, J=9.1 Hz, 1H), 7.10 (s, 1H), 6.81 (q, J=5.1 Hz, 1H), 4.80 (t, J=5.8 Hz, 1H), 3.90 (s, 3H), 3.83 (q, J=7.0 Hz, 1H), 3.22-3.10 (m, 1H), 2.95-2.85 (m, 1H), 2.15 (dt, J=14.0, 7.1 Hz, 1H), 2.09-1.99 (m, 2H), 1.61-1.52 (m, 4H), 1.44 (d, J=5.3 Hz, 3H), 1.05 (t, J=6.5 Hz, 2H), 0.87 (d, J=6.8 Hz, 3H), 0.85 (d, J=6.6 Hz, 3H). $^{13}$C NMR (101 MHz, $CDCl_3$) δ 171.72, 156.57, 153.33, 134.15, 132.62, 128.28, 127.87, 126.06, 125.21, 125.10, 117.86, 104.53, 88.61, 54.23, 44.39, 43.10, 40.17, 35.92, 32.24, 28.66, 24.03, 21.57 (2), 18.64, 17.38.

Examples 2

Synthesis of Gabapentin-GHB Conjugate

This example generally provides the synthesis of a GABA-analog-γ hydroxybutyric acid (GHB) conjugate, and more specifically, a gabapentin-GHB conjugate.

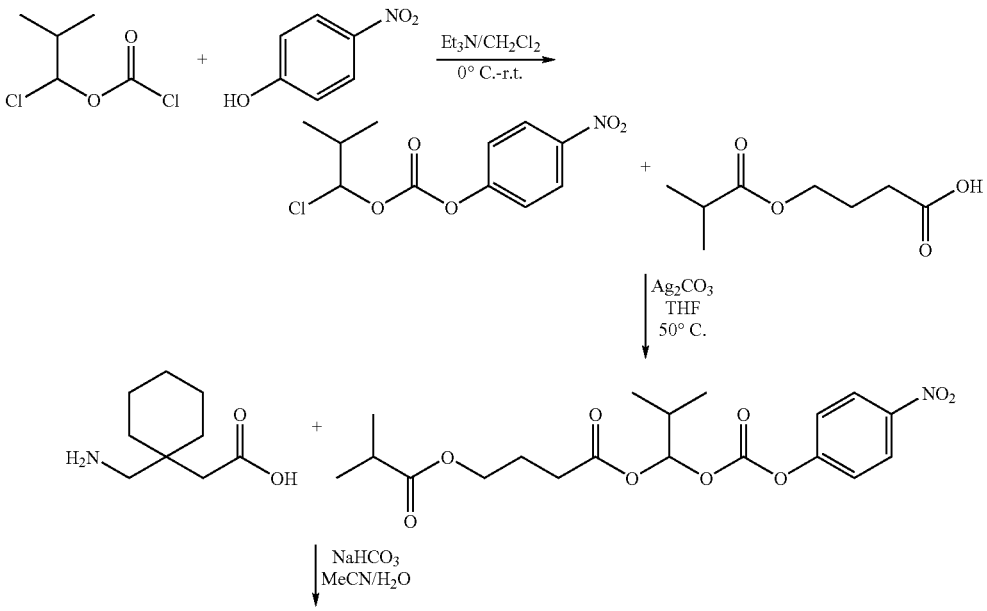

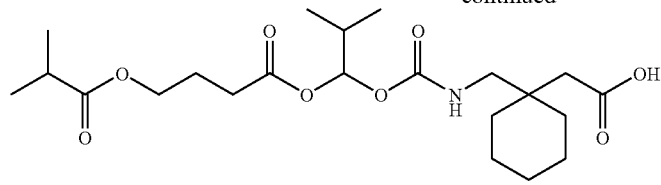
10
Examples 3
Synthesis of GABA$_B$ Agonist-Morphine Conjugate
This example provides the synthesis of a GABA receptor agonist-opiate analgesic drug conjugate, and more specifically, a GABA$_B$ agonist-morphine conjugate.
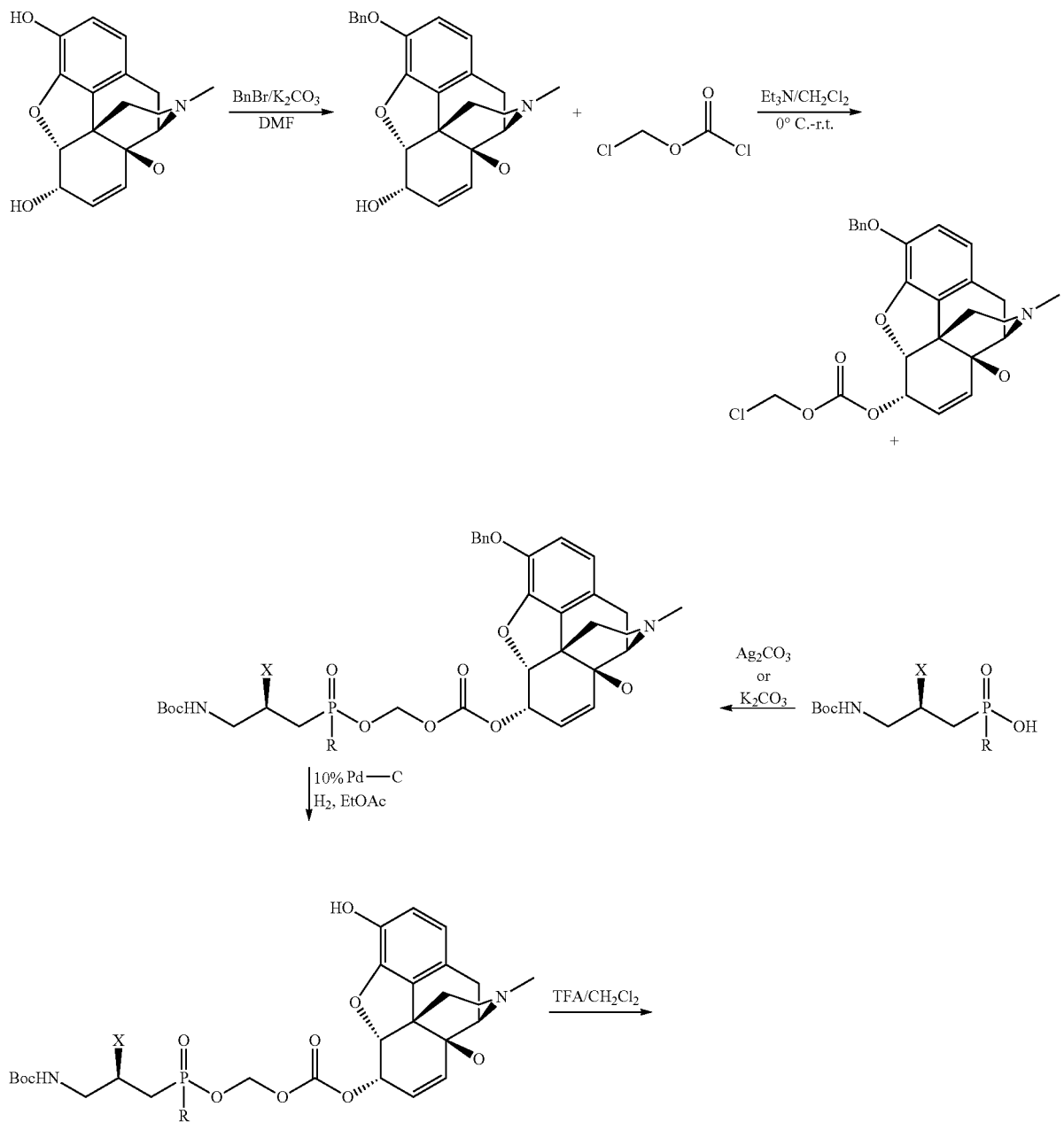

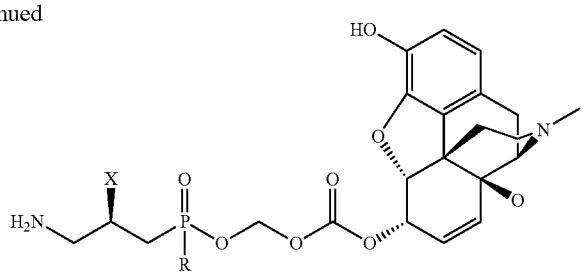

X = —F, —OH; R = —H, —Me, —CHF$_2$;

The examples provided hereinabove are to be considered as illustrative and not restrictive, and the invention is not to be limited to the details given herein, but may be modified within the scope and equivalents of the invention.

Example 4

In Vitro Determination of Caco-2 Cellular Permeability of GABA-Drug Conjugates

The passive permeability of the GABA-Drug conjugates of the current invention is assessed in vitro using standard methods well known in the art (See, e.g., Stewart, et al., *Pharm. Res.*, 1995, 12, 693). For example, passive permeability is evaluated by examining the flux of a GABA-Drug across a cultured polarized cell monolayer (e.g., Caco-2 cells). Caco-2 cells obtained from continuous culture (passage less than 28) are seeded at high density onto Transwell polycarbonate filters. Cells are maintained with DMEM/10% fetal calf serum+ 0.1 mM nonessential amino acids+2 mM L-Gln, 5% CO$_2$/ 95% O$_2$, 37° C. until the day of the experiment. Permeability studies are conducted at pH 6.5 apically (in 50 mM MES buffer containing 1 mM CaCl$_2$, 1 mM MgCl$_2$, 150 mM NaCl, 3 mM KCl, 1 mM NaH$_2$PO4, 5 mM glucose) and pH 7.4 basolaterally (in Hanks' balanced salt solution containing 10 mM HEPES) in the presence of efflux pump inhibitors (250 μM MK-571, 250 uM Verapamil, 1 mM Ofloxacin). Inserts are placed in 12 or 24 well plates containing buffer and incubated for 30 min at 37C° . Prodrug (200 μM) is added to the apical or basolateral compartment (donor) and concentrations of prodrug and/or released parent drug in the opposite compartment (receiver) are determined at intervals over 1 hour using LC/MS/MS. Values of apparent permeability ($P_{app}$) are calculated using the equation:

$$P_{app} = V_r(dC/dt)/(AC_o)$$

Here $V_r$ is the volume of the receiver compartment in mL; dC/dt is the total flux of GABA-Drug and parent drugs (μM/ s), determined from the slope of the plot of concentration in the receiver compartment versus time; $C_o$ is the initial concentration of GABA-Drug conjugates in μM; A is the surface area of the membrane in cm$^2$. Preferably, GABA-Drug conjugate with significant transcellular permeability demonstrate a value of $P_{app}$ of $\geq 1 \times 10^{-6}$ cm/s and more preferably, a value of $P_{app}$ of $\geq 1 \times 10^{-5}$ cm/s, and still more preferably a value of $P_{app}$ of $\geq 5 \times 10^{-5}$ cm/s.

Example 5

Chemical Stability

For the chemical stability studies, buffers are prepared at pH 2.0 (using 0.1M potassium phosphate and 0.5M NaCl), pH 7.4 and pH 8.0 (using 0.1M Tris-HCl and 0.5M NaCl). Compounds (5 μM) are incubated with buffers at 37° C. for 1 hour in a temperature controlled HPLC autosampler. Samples are injected at zero and 1 hour post-addition. Samples are analyzed by LC/MS/MS as described below.

Example 6

Metabolic Stability

Plasma Stability: Compounds (5 μM) are incubated with 90% rat or human plasma at 37° C. for 1 hour. Samples are obtained at zero and 1 hour post-addition and are immediately quench with methanol to prevent further conversion. Quenched samples are frozen and maintained at −80° C. prior analysis. Samples are analyzed by LC/MS/MS as described below.

Liver Homogenate: Compounds (5 μM) are incubated with rat or human liver S9 at 0.5 mg protein/mL in the presence of 1mM NADPH at pH 7.4 and at 37° C. for 1 hour. Samples are obtained at zero and 1 hour post-addition and are immediately quench with methanol to prevent further conversion. Quenched samples are frozen and maintained at −80° C. prior analysis. Samples are analyzed by LC/MS/MS as described below.

Caco-2 Cell Homogenate: Caco-2 cells are grown in flasks over 21 days. Cells are then rinsed/scraped off into ice-cold 10 mM sodium phosphate/0.15 M potassium chloride, pH 7.4. Cells will be lysed by sonication at 4° C. using a probe sonicator and centrifuged at 9,000×g for 20 min at 4° C. and the resulting supernatant (Caco-2 cell homogenate S9 fraction) aliquots are transferred into 0.5 mL vials and stored at −80° C. prior to use. For stability studies, compounds (5 μM) are incubated with Caco-2 S9 (0.5 mg protein/mL) at pH 7.4 and 37° C. for 1 hr. Samples are obtained at zero and 1 hr post-addition and are immediately quenched with methanol to prevent further conversion. Quenched samples are frozen and maintained at −80° C. prior to analysis. Samples are analyzed by LC/MS/MS as described below.

Pancreatin: Compounds (5 μM) are incubated with porcine pancreatin (10 mg/mL in pH 7.5 buffer) at 37° C. for 1 hour. Samples are obtained at zero and 1 hour post-addition and are immediately quench with methanol to prevent further conversion. Quenched samples are frozen and maintained at −80° C. prior analysis. Samples are analyzed by LC/MS/MS as described below.

Drug Conjugates Metabolism in Various Species: The drug conjugate (10 μM) is incubated with plasma, intestinal S9, lung S9, liver S9 and kidney S9 from rats, dogs, monkeys and humans at 37° C. for 1 hour. All preparations should contain 1 mg protein/mL. Samples are obtained at zero and intervals over 1 hour post addition and are immediately quenched with methanol to prevent further conversion. Quenched samples are then frozen and maintained at −80° C. prior to analysis. Samples are analyzed by LC/MS/MS as described below. The rate of conversion of drug conjugates to parent drugs in each matrix is calculated in pmol/min/mg protein.

Inhibition of Specific CYP450 Isoforms by Drug Conjugates: The lead candidate of GABA-Drug conjugate is tested for inhibition of CYP450 isoforms. The ability of drug conjugate to inhibit cytochrome P450-mediated metabolism is examined by standard methods using specific CYP450 isoforms expressed in bacculosomes (Supersomes™). The experimental conditions for each isoform are listed below. Standard substrates are employed that generate fluorescent metabolites. Experiments are conducted in a 96 well format. All incubations included an NADPH cofactor mix. The final concentration of CYP450 protein in each incubation should be between 2.5 to 5.0 pM. All compounds including positive control compounds are serially diluted in the solution of NADPH generation system to give final concentration of up to 400 uM. The resulting solutions are incubated with a specific CYP450 isoform and the related substrate at 37° C. for 15 to 45 minutes. A stop solution (80% acetonitrile/20% 0.5 M Tris base) is added to terminate the reaction. The samples are analyzed using a FlexStation fluorescence plate reader.

The percent inhibition of the formation of product is determined for each drug conjugate concentration and for control inhibitors. Blank values are subtracted from the sample wells to obtain the net fluorescence signal. The concentrations of drug conjugate that bracketed 50% inhibition ($C_{High}$ and $C_{Low}$) are determined. The $IC_{50}$ values for inhibition of each specific isoform are then determined from the bracketing concentrations and corresponding percent inhibition values via linear interpolation as follows:

$$IC_{50} = (50\% - \% I_{Low})/(\% I_{High} - \% I_{Low}) \times (C_{High} - C_{low}) + C_{Low}$$

where $C_{Low}$ and $C_{High}$ are the concentrations bracketing 50% inhibition and % $I_{High}$ and % $I_{Low}$ are the corresponding percent inhibition values at the low and high concentrations, respectively. This is the calculation method recommended by the supplier of the Supersomes™.

CYP Isoforms (Standard Substrate): CYP3A4 (7-benzyloxytrifluoromethycoumarin); CYP1A2 (3-cyano-7-ethoxycoumarin); CYP2C9 (7-methoxytrifluoromethylcoumarin); CYP2C19 (3-cyano-7-ethoxycoumarin); CYP2D6 (3-[2-(N, N-diethyl-N-methylamino)ethyl]-7-methyoxy-4-methylcoumarin); CYP2E1 (7-methyoxy-4-trifluoromethylcoumarin).

Example 7

Uptake of GABA Analogs and Conjugated Analgesics Following Administration of GABA Analogs, Analgesics or GABA-Drug Conjugates Intracolonically in Rats Sustained release oral dosage forms, which release drug slowly over periods of 6-24 hours, generally release a significant proportion of the dose within the colon. Thus, drugs suitable for use in such dosage forms preferably exhibit good colonic absorption. This experiment is conducted to assess the suitability of GABA-Drug conjugates for use in an oral sustained release formulation.

Step A: Admiistration Protocol

Rats are obtained commercially and are pre-cannulated in the both the ascending colon and the jugular vein. Animals should be conscious at the time of the experiment. All animals are fasted overnight and until 4 hours post-dosing. The compounds of the interest are administered as a solution (in water or can be other solvent such as PEG 400) directly into the colon via the cannula at a dose of the desire. Blood samples (0.5 mL) are obtained from the jugular cannula at intervals over 8 hours and are quenched immediately by addition of acetonitrile/methanol to prevent further conversion of the GABA-Drug conjugates. Blood samples are analyzed as described below.

Step B: Sample Preparation for Colonic Absorbed Drug

In blank 1.5 mL eppendorf tubes, 300 μL of 50/50 acetonitrile/methanol and 20 μL of p-chlorophenylalanine are added as an internal standard.

1. Rat blood is collected at different time points and immediately 100 μL of blood is added into the eppendorf tube and vortexed to mix.
2. 10 μL of a GABA analogs or an analgesic drug standard solution (0.04, 0.2, 1, 5, 25, 100 μg/mL) is added to 90 μL of blank rat blood to make up a final calibration standard (0.004, 0.02, 0.1, 0.5, 2.5, 10 μg/mL). Then 300 μL of 50/50 acetonitrile/methanol is added into each tube followed by 20 μL of p-chlorophenylalanine.
3. Samples are vortexed and centrifuged at 14,000 rpm for 10 min.
4. Supernatant is taken for LC/MS/MS analysis.

Step C: LC/MS/MS Analysis

A LC/MS/MS spectrometer equipped with 10ADVp binary pumps and a CTC HTS-PAL autosampler is used in the analysis. A column of the choice is heated to 45° C. during the analysis. The mobile phase can be different solvent mixtures, such as 0.1% formic acid (A) and acetonitrile with 0.1% formic acid (B). The gradient condition can be varied depend on the compound analyzed. A TurbolonSpray source can be used on the LC/MS/MS instrument such as API 2000. The analysis may be done in both positive or negative ion mode and an MRM transition can be selected based on the analysis of the compounds. 20 μL of the samples is injected. The peaks can be integrated using Analyst 1.1 quantitation software. Following colonic administration of each of these GABA-Drug conjugates, the maximum plasma concentrations of GABA analogs and analgesic drugs ($C_{max}$), as well as the area under the GABA analogs and analgesic drugs plasma concentration vs. time curves (AUC) are compared to the parent drugs. A desired conjugates should provide both GABA analogs and analgesic drug with higher $C_{max}$ and greater AUC values than GABA analogs and analgesic itself This data demonstrates that compounds of the invention may be formulated as compositions suitable for enhanced absorption and/or effective sustained release of GABA analogs and analgesic drugs chosen to minimize dosing frequency due to rapid systemic clearance of these GABA analogs.

Example 8

Pharmacokinetics of Conjugated GABA Analogs or Conjugated Analgesics Following Intravenous Administration to Cynomolgus Monkeys GABA analogs or analgesic drugs are administered to four male cynomolgus monkeys as an aqueous solution by intravenous bolus injection into the saphenous vein at a desired dose. Blood samples are obtained from all animals at intervals over 24 hours post-dosing. Blood is processed immediately for plasma at 4° C. All plasma samples are subsequently analyzed for GABA analogs or analgesic drugs using the LC/MS/MS assay described above.

Example 9

Uptake of GABA Analogs or Conjugated Analgesic Drugs Following Administration of GABA Analogs or GABA-Drug Conjugates Intracolonically in Cynomolgus Monkeys GABA analogs, analgesic drugs and GABA-Drug conjugates are administered at a desired dose to groups of four male cynomolgus monkeys as either aqueous solutions or suspensions via bolus injection directly into the colon via an indwelling cannula. For colonic delivery, a flexible French catheter is inserted into the rectum of each monkey and extended to the proximal colon (approx. 16 inches) using fluoroscopy. Monkeys are lightly sedated by administration of Telazol/ketamine during dosing. A washout period of at least 5 to 7 days is allowed between treatments. Following dosing, blood samples are obtained at intervals over 24 hours and are immediately quenched and processed for plasma at 4° C. All plasma samples are subsequently analyzed for GABA analogs, analgesic drugs and intact GABA-Drug conjugates using the LC/MS/MS assay described above. Following colonic administration of GABA-Drug conjugates, the maximum plasma concentrations of GABA analogs and analgesic drugs ($C_{max}$), as well as the area under the GABA analogs and analgesic drugs plasma concentration vs. time curves (AUC) are significantly greater than that produced from colonic administration of GABA analog itself This data demonstrates that these GABA-Drug conjugates may be formulated as compositions suitable for enhanced absorption and/or effective sustained release of GABA analogs to minimize dosing frequency due to rapid systemic clearance of these GABA analogs.

Example 10

Uptake of GABA Analogs and Conjugated Analgesic Drugs Following Oral Administration of GABA-Drug Conjugates to Cynomolgus Monkeys The GABA-Drug conjugates are administered by oral gavage to groups of four male cynomolgus monkeys as either an aqueous solution or suspension respectively. Following dosing, blood samples are obtained at intervals over 24 hours and are immediately quenched and processed for plasma at 4° C. All plasma samples are subsequently analyzed for GABA analogs, analgesic drugs and intact GABA-Drug conjugates using the LC/MS/MS assay described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound comprising a first moiety, a second moiety, and a physiologically labile linker that covalently links the first moiety to the second moiety, wherein the first moiety is covalently linked via an amino terminus to the linker, wherein the first moiety is γ-aminobutyric acid (GABA) or an analog or derivative of GABA, the second moiety is a nonsteroidal anti-inflammatory drug (NSAID) or γ-hydroxybutyric acid (GHB) or an analog or derivative of GHB, and the linker has the structure of

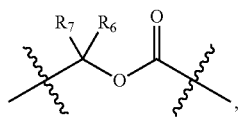

wherein $R_6$ and $R_7$ are independently selected from the group consisting of hydrogen, alkyl, substituted alkyl, acyl, substituted alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, arylalkyl, substituted arylalkyl, heteroarylalkyl and substituted heteroarylalkyl; wherein the second moiety is covalently linked to the linker via a carboxylic acid or a hydroxyl group.

2. The compound of claim 1, wherein the first moiety is a baclofen, vigabatrin, gabapentin, or pregabalin, or a γ-aminophosphinic acid derivative.

3. The compound of claim 1, wherein the compound is used in combination with at least one other therapeutic agent.

4. The compound of claim 3, wherein the at least one other therapeutic agent is selected from the group consisting of an anti-psychotic drug, an anxiolytic drug, an anti-depressant drug, an anti-convulsive drug, an antiparkinsonian drug, an acetylcholine esterase inhibitor, a MAO inhibitor, a selective serotonin reuptake inhibitor (SSRI), an N-methyl-D-aspartic acid (NMDA) antagonist, and a selective noradrenalin replace inhibitor.

5. A pharmaceutical composition comprising the compound of claim 1 and a pharmaceutically acceptable carrier.

6. The pharmaceutical composition of claim 5 further comprises at least one other therapeutic agent.

7. The pharmaceutical composition of claim 5, wherein the composition is for treating pain and/or a neurological disorder.

8. A kit for treating pain or a neurological disorder in a subject, the kit comprising the compound of claim 1, and instructions for using the kit.

9. The kit of claim 8, wherein the subject is an animal, preferably a human.

10. The kit of claim 8 further comprises at least one other agent for use in the treatment of pain or a neurological disorder.

11. The compound of claim 1, wherein the compound is

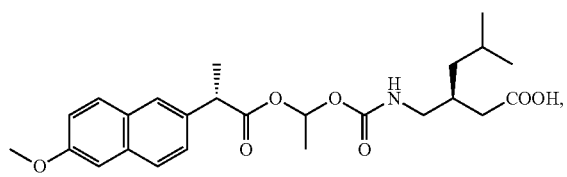

or a pharmaceutically acceptable salt thereof.

12. The compound of claim 1, wherein the compound is
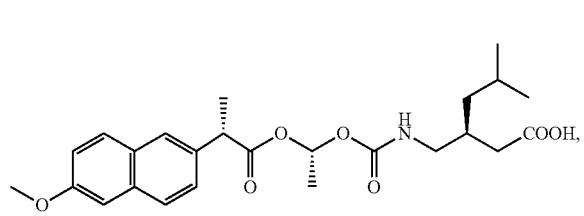
or a pharmaceutically acceptable salt thereof.
13. The compound of claim 1, wherein the compound is
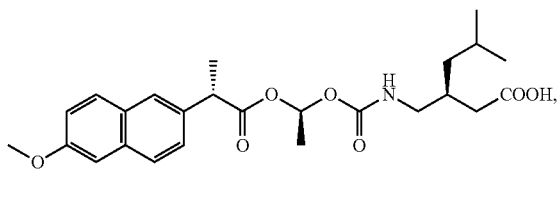
or a pharmaceutically acceptable salt thereof.
* * * * *